(12) United States Patent
James

(10) Patent No.: US 8,030,465 B2
(45) Date of Patent: Oct. 4, 2011

(54) NUCLEIC ACID LIGANDS TO COMPLEX TARGETS

(75) Inventor: Robert James, Wattle Park (AU)

(73) Assignee: Medimolecular Pty Ltd, Bedford Park (AU)

( * ) Notice: Subject to any disclaimer, the term of this patent is extended or adjusted under 35 U.S.C. 154(b) by 546 days.

(21) Appl. No.: 12/100,242

(22) Filed: Apr. 9, 2008

(65) Prior Publication Data

US 2010/0112554 A1   May 6, 2010

Related U.S. Application Data

(63) Continuation-in-part of application No. 10/746,339, filed on Dec. 29, 2003, now abandoned, which is a continuation-in-part of application No. PCT/AU02/00857, filed on Jun. 28, 2002.

(30) Foreign Application Priority Data

Jun. 29, 2001 (AU) ........................ PR5985
Mar. 28, 2002 (AU) ........................ 27754/02

(51) Int. Cl.
    *C07H 21/04* (2006.01)
(52) U.S. Cl. ..................................... 536/23.1
(58) Field of Classification Search ............. 536/23.1
    See application file for complete search history.

(56) References Cited

U.S. PATENT DOCUMENTS

| | | | |
|---|---|---|---|
| 5,270,163 A | 12/1993 | Gold et al. |
| 5,670,637 A | 9/1997 | Gold et al. |
| 5,686,242 A | 11/1997 | Bruice et al. |
| 5,696,249 A | 12/1997 | Gold et al. |
| 5,843,653 A | 12/1998 | Gold et al. |
| 6,110,900 A | 8/2000 | Gold et al. |
| 6,333,137 B1 | 12/2001 | Dickinson et al. |

FOREIGN PATENT DOCUMENTS

| | | |
|---|---|---|
| EP | 0328829 A2 | 8/1989 |
| WO | WO-91/19813 A1 | 12/1991 |
| WO | WO-92/05285 A1 | 4/1992 |
| WO | WO-92/14843 A1 | 9/1992 |
| WO | WO-94/08050 A1 | 4/1994 |
| WO | WO-94/09158 A1 | 4/1994 |
| WO | WO-95/07364 A1 | 3/1995 |
| WO | WO-95/30775 A1 | 11/1995 |
| WO | WO-96/08003 A1 | 3/1996 |
| WO | WO-96/27605 A1 | 9/1996 |
| WO | WO-96/34874 A1 | 11/1996 |
| WO | WO-96/34875 A1 | 11/1996 |
| WO | WO-97/38134 A1 | 10/1997 |
| WO | WO-98/34110 A1 | 8/1998 |
| WO | WO-99/07724 | 2/1999 |
| WO | WO-99/28497 A1 | 6/1999 |
| WO | WO-99/38134 A1 | 7/1999 |
| WO | WO-00/56930 A1 | 9/2000 |
| WO | WO-01/09380 A1 | 2/2001 |

OTHER PUBLICATIONS

Morris et al., Proc. Natl. Acad. Sci. USA, vol. 95, pp. 2902-2907 (Mar. 1998).
Blank et al., J. Biol Chem., vol. 276, No. 19, pp. 16464-16468 (May 11, 2001).
Vant-Hull et al., J. Mol. Biol., 278, 579-597 (1998).
Ellington et al., "Selection of RNAs with Ligand-specific Binding Activity from Pools of Random Sequence Molecules," Abstracts of papers presented at the 1990 meeting on RNA Processing, May 16-20, 1990, p. 84.
Famulok et al., Curr. Top. Microbiol. Immunol. 243:123-136 (1999).
Robertson et al., Nature, vol. 344, pp. 467-468 (Mar. 29, 1990).
Kinzler et al., Nucleic Acids Research, vol. 17, No. 10, 3645-3653 (1989).
Oliphant et al., Nucleic. Acids Research, vol. 16, No. 15, 7673-7683 (1988).
Joyce et al., Nucleic Acids Research, vol. 17, No. 2, 711-722 (1989).
Thiesen et al., Nucleic Acids Research, vol. 18, No. 11, 3203-3209 (1990).
Joyce et al., Gene, 82(1), pp. 83-87 (1989).
Oliphant et al., Gene, 44(2-3), pp. 177-183 (1986).
Oliphant et al., Methods in Enzymology, 155:568-582 (1997).
Oliphant et al., Molecular and Cellular Biology, vol. 9, No. 7, pp. 2944-2949 (1989).
Ellington et al., Nature, vol. 346, pp. 818-822 (Aug. 30, 1990).
Tuerk et al., Science, vol. 249, pp. 505-510 (Aug. 1990).

*Primary Examiner* — Gary Benzion
*Assistant Examiner* — Cynthia Wilder
(74) *Attorney, Agent, or Firm* — Birch, Stewart, Kolasch & Birch, LLP

(57) ABSTRACT

The present invention relates to a nucleic acid ligands capable of binding to one or more target molecules in a complex mixture.

17 Claims, 5 Drawing Sheets

SEQUENCE LISTING

```
<160> NUMBER OF SEQ ID NOS: 6

<210> SEQ ID NO 1
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 1
gggagctcag aataaacgct caaggaacag caagatacgg tcaccgaaca tagcgcacca      60
caggcaca                                                              68

<210> SEQ ID NO 2
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 2
gggagctcag aataaacgct caacaaaaga ctatccagcg acacgcaatc tcaagcaaca      60
```

```
gaggacag                                                                   68

<210> SEQ ID NO 3
<211> LENGTH: 85
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(65)
<223> OTHER INFORMATION: n is a, c, g, or t

<400> SEQUENCE: 3
agctcagaat aaacgctcaa nnnnnnnnnn nnnnnnnnnn nnnnnnnnnn nnnnnnnnnn     60
nnnnnttcga catgaggccc ggatc                                           85

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
gatccgggcc tcatgtcga                                                  19

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 5
gggagctcag aataaacgct caa                                             23

<210> SEQ ID NO 6
<211> LENGTH: 88
<212> TYPE: DNA
<213> ORGANISM: Artificial Sequence
<220> FEATURE:
<223> OTHER INFORMATION: Synthetic polynucleotide

<400> SEQUENCE: 6
gggagctcag aataaacgct caaggaacag caagatacgg tcaccgaaca tagcgcacca     60
caggcacatt cgacatgagg cccggatc                                        88
```

NUCLEIC ACID LIGANDS TO COMPLEX TARGETS

This application is a Continuation-in-Part of co-pending application Ser. No. 10/746,339, filed on Dec. 29, 2003, and for which priority is claimed under 35 U.S.C. §120. Application Ser. No. 10/746,339 is a Continuation-in-Part of Application No. PCT/AU02/00857, filed on Jun. 28, 2002, which designated the United States on which priority is claimed under 35 U.S.C. §120. This application also claims priority under 35 U.S.C. §119(a) on Australian Patent Application No. PR 5985, filed Jun. 29, 2001 and Australian Patent Application No. 27754/02, filed Mar. 28, 2002. The entire contents of all are hereby incorporated by reference.

FIELD OF THE INVENTION

The present invention relates to methods for identifying nucleic acid ligands to specific molecules in complex mixtures. The present invention also relates to nucleic acid ligands isolated by such methods.

BACKGROUND OF THE INVENTION

Many biological and chemical systems are composed of a large number of different interacting molecular species. The manner in which many of these molecules interact with each other determines the properties and functions of the particular system. For example, the function and properties of a particular biological system are due to the many and varied interactions that occur between the proteins, nucleic acids and other molecules that make up the system.

In order to understand how such complex systems function, it is necessary to define the individual interactions that occur between the different molecular species. A first step in defining these interactions is the identification of what molecular species are present in a system, and at what concentration they exist to exert their actions.

An improved understanding of the molecular species present in a complex system, and at what concentrations they exist, is also important in determining how some complex systems undergo a transition from one state to another state. For example, such considerations are important in understanding how the change from a normal state to a diseased state occurs for some cell types. An understanding of the identity and concentration of the molecular species present in a system is also important in terms of diagnosis and prognosis. For example, the transformation of a normal tissue to a pre-malignant tissue, and ultimately to a malignant one, may be able to be identified by an improved understanding of the presence and concentration of the molecular species present at any particular time in the cells of interest.

A powerful tool for the identification of the molecular species present in a complex mixture is the use of probe molecules that have the capacity to bind or interact with a particular molecule of interest. For example, antibodies may be used to identify specific antigens in complex mixtures of antigens. Naturally occurring ligands to a molecule (or engineered variants thereof) may be detectably labelled and used to identify their targets in complex mixtures of receptor molecules. Nucleic acids complementary to another specific nucleic acid may be used to identify and characterise the specific nucleic acid in a complex mixture of nucleic acids.

Accordingly, the generation of ligands with specificity to new or important target molecules is an important tool for research, diagnosis and treatment. However, the generation of new ligands to a specific target molecule is often problematic.

In some cases, rational design of new ligands may be effective. In such instances a detailed understanding of the three dimensional structure of the relevant part of the target molecule is usually required. However, many target molecules (for example proteins) have complex structures, making the rational design of new ligands to the molecule difficult.

In some instances it is possible to identify new ligands to a target molecule without knowledge of the structure of the target molecule. In this case, the ability to identify new ligands is usually dependent upon the ability to generate a large number of molecules of different structure, a proportion of which may have the capacity to bind to a target molecule with useful affinity. For example, the generation of antibodies in vivo relies on such a principle. However, for the generation of antibodies specific to a particular target molecule it is usually necessary to first isolate the target antigen and/or screen a large number of monoclonal antibodies for binding to the target antigen. In addition, the use of antibodies as tools is often limited by the capacity to generate and isolate antibodies against specific types of target antigens, and the fact that the generation and testing of antibodies is a time consuming and labour intensive process.

Single stranded nucleic acids also have the capacity to form a multitude of different three dimensional structures. Indeed, single stranded nucleic acids may have a three dimensional structural diversity not unlike proteins. The three dimensional structure adopted by any one single stranded nucleic acid is dependent upon the primary sequence of nucleotides, and ultimately is the result of the numerous types of intra-molecular interactions that occur between atoms present in the molecule and inter-molecular interactions that occur between atoms present in the molecule and the surrounding solvent. The three dimensional structure will also depend upon the kinetics and thermodynamics of folding of any one structure.

Because single stranded nucleic acids have the capacity to form a multitude of different three dimensional structures, they may also be potential ligands to a large variety of different types of target molecules. Single stranded nucleic acids that have the capacity to bind to other target molecules are generally referred to as aptamers. In fact, given the structural diversity possible with single stranded nucleic acids; it may be possible to isolate a single stranded nucleic acid with a useful binding affinity to any molecule of interest.

In this regard, chemical synthesis of nucleic acids allows the generation of a pool of large numbers of single stranded nucleic acids of random nucleotide sequence. If the complexity of the pool of single stranded molecules generated by chemical synthesis is sufficient, it may be possible to isolate a unique nucleic acid ligand to any specific molecule. For example, SELEX (systematic evolution of ligands by exponential enrichment) is a technique that allows the isolation of specific nucleic acid ligands from a starting pool of candidate single stranded nucleic acids. By a process of reiterated steps of binding nucleic acids to a target molecule, isolation of the bound nucleic acids and subsequent amplification, nucleic acid ligands to a specific molecule may be quickly and easily identified.

However, a deficiency in the use of single stranded nucleic acid targets has been the inability to identify and use single stranded nucleic acid ligands to complex mixtures of molecules, as for example are present in cellular extracts. The large number of molecules present in the mixture, and the variety of interactions of varying affinity that are possible between molecules in the mixture and nucleic acid ligands, has made the identification and use of specific nucleic acid ligands to such mixtures problematic.

For example, the isolation of a specific nucleic acid ligand to a specific molecule by a process such as SELEX using purified, or even partially purified targets, does not necessarily result in a nucleic acid ligand that is effective in binding to the specific molecule when that molecule is present in a complex mixture of other potential target molecules. It would be advantageous to isolate nucleic acid ligands that can bind to specific molecules present in complex mixtures. It would also be advantageous to use such ligands to screen for differences in the concentration of specific target molecules between different sets of complex mixtures.

In addition, a further deficiency with the identification of nucleic acid ligands to complex mixtures has been the inability to readily produce a library of different nucleic acid ligands to the complex mixture. For example, it would ultimately be advantageous for many reasons to be able to readily isolate a unique nucleic acid ligand to every biologically significant molecule in a complex mixture.

To produce such a library of nucleic acid ligands by existing SELEX techniques would require the isolation of a specific target molecule present in the complex mixture and the independent isolation of a nucleic acid ligand to that specific molecule. In such a way, by repeating this process for each newly isolated molecule present in the complex mixture, a library of nucleic acid ligands to a number of different molecules in the complex mixture could be built up. However, not only is such a sequential manner of isolating nucleic acid ligands laborious and time consuming, the ligands so isolated may not be effective in binding to their specific target molecules, when those molecules are present in a complex mixture of other molecules.

The present invention relates to methods for the isolation of nucleic acid ligands that are capable of binding to target molecules present in complex mixtures.

SUMMARY OF THE INVENTION

The present invention provides a method for isolating a nucleic acid ligand capable of binding to a target molecule in a complex mixture, the method including the steps of:
(a) providing a pool of candidate nucleic acid ligands;
(b) providing a pool of target molecules;
(c) allowing the nucleic acid ligands to bind to the target molecules;
(d) isolating nucleic acid ligands bound to the target molecules;
(e) amplifying the isolated nucleic acid ligands;
(f) reiterating steps (a) to (e) using the amplified nucleic acid ligands as the pool of candidate nucleic acid ligands, wherein the steps are reiterated until a final pool of nucleic acid ligands is obtained with a desired level of binding specificity to the pool of target molecules; and
(g) isolating a specific nucleic acid ligand from the final pool of nucleic acid ligands, wherein the specific nucleic acid ligand is capable of binding to a target molecule in a complex mixture.

The present invention also provides a method for isolating a pool of nucleic acid ligands capable of binding to one or more target molecules in a complex mixture, the method including the steps of:
(a) providing a pool of candidate nucleic acid ligands;
(b) providing a first pool of target molecules;
(c) providing a second pool of target molecules, wherein the second pool of target molecules may be isolated from the first pool of target molecules, and wherein the second pool of target molecules differs from the first pool of target molecules in that one or more of the target molecules in the second pool is present at a higher concentration than that present in the first pool of target molecules;
(d) allowing the nucleic acid ligands to bind to the first and second pools of target molecules, wherein the first and second pool of target molecules are in the presence of one another;
(e) isolating the nucleic acid ligands bound to the second pool of target molecules;
(f) amplifying the isolated nucleic acid ligands bound to the second pool of target molecules;
(g) reiterating steps (a) through (f) using the amplified nucleic acid ligands as the pool of candidate nucleic acid ligands, wherein the steps are reiterated until a final pool of nucleic acid ligands is obtained with a desired level of binding specificity to the second pool of target molecules; and
(h) isolating the final pool of nucleic acid ligands so produced, wherein the final pool of nucleic acid ligands allows the differentiation of a test pool of molecules from a control pool of molecules.

The present invention further provides a method for isolating a plurality of individual nucleic acid ligands capable of binding to a plurality of different target molecules in a complex mixture of molecules, the method including the steps of:
(a) providing a pool of candidate nucleic acid ligands;
(b) providing a pool of target molecules, wherein the target molecules in the pool may be isolated;
(c) allowing the nucleic acid ligands to bind to the target molecules;
(d) isolating the nucleic acid ligands bound to the pool of target molecules;
(e) amplifying the isolated nucleic acid ligands;
(f) isolating an individual nucleic acid ligand from the amplified nucleic acid ligands;
(g) using the individual nucleic acid ligand to deplete the pool of target molecules of a specific molecule;
(h) reiterating steps (a) to (g) using the successively depleted pool of target molecules as the starting pool of target molecules for each cycle of reiteration, wherein the steps are reiterated until a plurality of individual nucleic acid ligands is identified.

It has been determined by the applicant that a nucleic acid ligand may be isolated that has the capacity to bind to a target molecule when the target molecule is present in a complex mixture of other molecules. Rather than isolating a nucleic acid ligand that has the capacity to bind to a purified or semi purified target molecule and then testing whether the nucleic acid so isolated has the capacity to bind to the target molecule when the target molecule is present in a complex mixture, it has been determined that the isolation of nucleic acid ligands that have the capacity to bind to a target molecule in a complex mixture may be achieved directly by allowing a pool of candidate single stranded nucleic acids to bind to the complex mixture itself.

This ability to isolate nucleic acid ligands to target molecules in a complex mixture may be utilised to isolate a pool of nucleic acid ligands that allows the differentiation of a test pool of molecules from a control pool of molecules. In this regard it has been further determined that the ability to isolate a pool of nucleic acid ligands capable of the differentiation of a test pool of molecules from a control pool of molecules may be achieved by a reiterative process of binding and amplification of the nucleic acid: ligands to a pool of target molecules, provided that the reiterated steps of binding are performed in the presence of another pool of molecules that differs in the concentration of one or more target molecules.

Without being bound by theory, it appears that any small differences in the concentration of molecules between a test pool of molecules and a control pool of molecules are magnified by the reiterated cycles of binding and amplification, and after sufficient reiterations, resulting in a final population of nucleic acids that is able to distinguish between a test pool of molecules and a control pool of molecules.

The ability to isolate nucleic acid ligands to target molecules in a complex mixture may also be utilised to isolate a plurality of individual nucleic acid ligands capable of binding to a plurality of specific target molecules in a complex mixture of molecules, by a reiterative process of binding a pool of nucleic acid ligands to a pool of target molecules, isolating the bound nucleic acid ligands, selecting an individual nucleic acid ligand, and using this nucleic acid ligand to deplete the complex mixture of the target molecule. In this way it is possible to readily isolate a plurality of nucleic acid ligands to a large number of target molecules in a complex mixture.

Various terms that will be used throughout this specification have meanings that will be well understood by a skilled addressee. However, for ease of reference, some of these terms will now be defined.

The term "nucleic acid ligand" as used throughout the specification is to be understood to mean any single stranded deoxyribonucleic acid or ribonucleic acid that may act as a ligand for a target molecule. The term includes any nucleic acid in which a modification to the sugar-phosphate backbone or a modification to the structure of the bases has been made so as to improve the capacity of the nucleic acids to act as ligands, or any other step that improves the ability to isolate, amplify or otherwise use the ligands.

The term "target molecule" as used throughout the specification is to be understood to mean any target molecule to which a nucleic acid ligand may bind. For example, target molecules may include proteins, polysaccharides, glycoproteins, hormones, receptors, lipids, small molecules, drugs, metabolites, cofactors, transition state analogues and toxins, or any nucleic acid that is not complementary to its cognate nucleic acid ligand.

The term "pool" as used throughout the specification is to be understood to mean a collection of two or more different molecules.

The term "complex mixture" as used throughout the specification is to be understood to mean a collection of two or more different target molecules. The term includes any collection of different target molecules that may be derived from a biological or non-biological source.

Examples of a complex mixture derived from a biological source include proteins, nucleic acids, oligosaccharides, lipids, small molecules (or any combination of these molecules) derived from the following sources: a cell or any part thereof, groups of cells, viral particles (or any part thereof), tissue or organ. Examples of a complex mixture from a non-biological source include complex mixtures resulting from chemical reactions.

The term "isolated" as used throughout the specification is to be understood to mean any process that results in a partial or substantial purification, in that the isolation process provides an enrichment of the species being isolated.

The term "first pool of target molecules" as used throughout the specification is to be understood to mean a first population of two or more different target molecules.

The term "control pool of molecules" as used throughout the specification is to be understood to mean a population of molecules that provides a reference population of molecules against which a change in another population is to be measured. The first pool of target molecules may be identical or similar to a control pool of molecules.

The term "second pool of target molecules" as used throughout the specification is to be understood to mean a second population of two or more different target molecules, the second population having one or more target molecules present at higher concentration and/or structurally different, than present in a first population of molecules.

The term "test pool of molecules" as used throughout the specification is to be understood to mean a population of molecules in which a change in the concentration of one or more molecular species is to be measured. The second pool of target molecules may be identical or similar to a test pool of molecules.

The term "deplete" as used throughout the specification is to be understood to mean a process by which the concentration of a specific target in a complex mixture of molecules is reduced to an extent that the concentration of the specific molecule will not provide a substantial target for the binding of nucleic acid ligands.

BRIEF DESCRIPTION OF THE FIGURES

FIG. 4A is a bright field image and FIG. 4B is a fluorescence image from one case. FIG. 4C is a bright field image and FIG. 40 is a fluorescence image from a separate case. There is almost a complete absence of aptamer binding labeling apart from a 'random' dot-like background labeling, which is quite distinct from the densely punctuate staining observed in the malignant cells (see FIGS. 1 to 3) cases.

GENERAL DESCRIPTION OF THE INVENTION

Figure 1A:
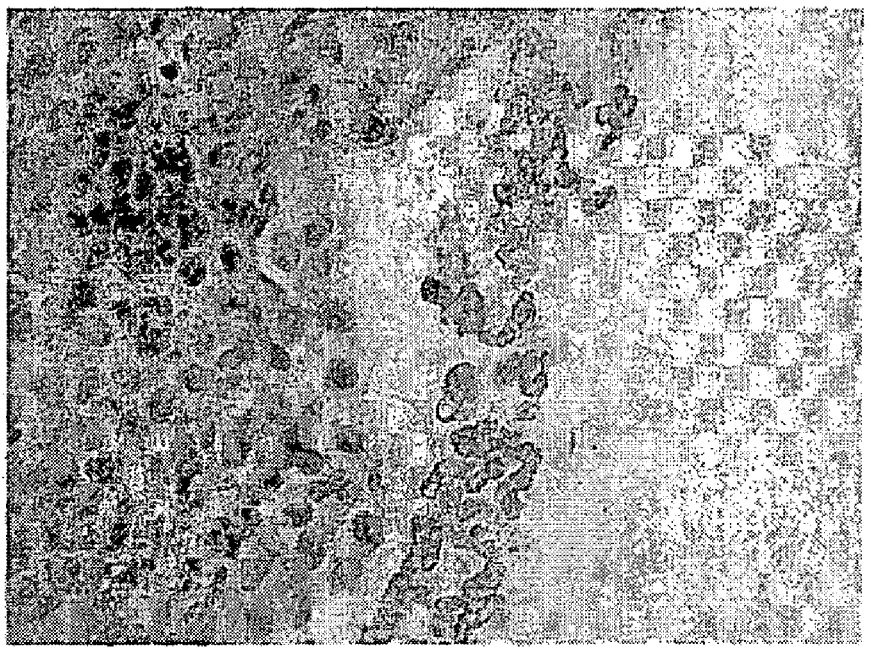
FIG. 1 shows staining of an epithelioid mesothelioma tissue section with aptamer MTA R72. A bright field image of an epithelioid mesothelioma is shown in the top panel (FIG. 1A) and a fluorescence image showing staining with aptamer MTA R72 is shown in the lower panel (FIG. 1B). Predominantly nuclear staining is seen with the aptamer MTA R72. Non cancerous cells contained within the border in the lower panel do not stain with the aptamer whereas the underlying tumour cells are positive.

As mentioned above, in one embodiment the present invention provides a method for isolating a nucleic acid ligand capable of binding to a target molecule in a complex mixture, the method including the steps of:

(a) providing a pool of candidate nucleic acid ligands;
(b) providing a pool of target molecules;
(c) allowing the nucleic acid ligands to bind to the target molecules;
(d) isolating nucleic acid ligands bound to the target molecules;
(e) amplifying the isolated nucleic acid ligands;
(f) reiterating steps (a) to (e) using the amplified nucleic acid ligands as the pool of candidate nucleic acid ligands, wherein the steps are reiterated until a final pool of nucleic acid ligands is obtained with a desired level of binding specificity to the pool of target molecules; and
(g) isolating a specific nucleic acid ligand from the final pool of nucleic acid ligands, wherein the specific nucleic acid ligand is capable of binding to a target molecule in a complex mixture.

The ability to isolate a nucleic acid ligand capable of binding to a target molecule in a complex mixture allows the use of such ligands to detect and determine the concentration of target molecules in a complex mixture of molecules. The benefits of a nucleic acid ligand with such properties for diagnostic, research and treatment purposes are readily apparent. For example, such nucleic acids ligands may be used for the identification of whether a group of cells has acquired a new phenotype, such as a cancerous or pre-cancerous phenotype, by using the nucleic acid ligands to determine the concentration of important target molecule in the cells.

In addition, nucleic acids with the capacity to bind to target molecules in a complex mixture are more likely to have possible therapeutic applications, because of their ability to bind to their target in amongst a myriad of other potential targets in a complex mixture.

The nucleic acid ligands according to the present invention may be based on either deoxyribonucleic acids or ribonucleic acids. The nucleic acid ligands may also contain modifications to the sugar-phosphate backbone, modifications to the 5' and/or 3' ends, modifications to the 2' hydroxyl group, the use of non-naturally occurring bases, or the use of modified bases derived from naturally or non-naturally occurring bases.

The nucleic acids according to the present invention may also be circular nucleic acid ligands or a nucleic acid ligand that is conformationally constrained by intra molecular linkages.

The size of the nucleic acid ligands may be selected with regard to a number of parameters, including the desired complexity of the candidate pool and any structural and/or sequence constraints. In one embodiment, the pool of candidate nucleic acid ligands has an average size in the range from 30 to 150 nucleotides. In one specific embodiment, the average size is in the range from 50 to 100 nucleotides, such as the average size being 85 nucleotides.

The pool of candidate nucleic acid ligands may be generated by a method well known in the art, so long as the candidate pool generated is of sufficient complexity to allow the isolation of one or more nucleic acid ligands with the desired properties. In one embodiment, the pool of candidate nucleic acid ligands is generated by a method including the step of chemical synthesis. In one embodiment, the pool of candidate nucleic acid ligands will be generated by a method including chemical synthesis allowing the incorporation of one or more random nucleotides at a desired number of positions in the final oligonucleotides that result from the synthesis.

In one embodiment, the randomised section has a size in the range from 10 to 100 bases. In one specific embodiment, the randomised section has a size in the range from 30 to 80 bases, for example, the randomised section is 45 bases in length.

In one embodiment, each of the nucleic acid ligands in the pool of candidate nucleic add ligands includes a constant section of nucleotide sequence to allow amplification by polymerase chain reaction or to facilitate cloning.

The candidate pool may also be a pool of previously selected nucleic acid ligands. The candidate pool may also be a chemically synthesized pool of single stranded nucleic acids that has been further mutagenised by a method well known in the art or a previously selected pool of nucleic acid ligands that has been further mutagenised by a method well known in the art.

Target molecules may include proteins, polysaccharides, glycoproteins, hormones, receptors, lipids, small molecules, drugs, metabolites, cofactors, transition state analogues and toxins, or any nucleic acid that is not complementary to its cognate nucleic acid ligand.

The source of the pools of target molecules according includes cellular extracts derived from cell populations, group of cells, tissues or organs; whole cells; viral particles (or parts thereof); or chemical mixtures. Cellular extracts include extracts derived from tissues, including tissue sections, chemically preserved tissues such as formalin fixed tissue sections. In one embodiment, the source of the pool of target molecules is a cellular extract. In one specific embodiment, the cellular extract is derived from human cells. Cellular extracts may be prepared by methods well known in the art.

In one embodiment, the cellular extract is derived from cells selected from one or more of the following types of tissue: colorectal tissue, breast tissue, cervical tissue, uterine tissue, renal tissue, pancreatic tissue, esophageal tissue, stomach tissue, lung tissue, brain tissue, liver tissue, bladder tissue, bone tissue, prostate tissue, skin tissue, ovary tissue, testicular tissue, muscle tissue or vascular tissue. These tissues may further contain cells that are normal (non-cancerous), pre-cancerous (having acquired some but not all of the cellular mutations required for a cancerous genotype) or cancerous cells (malignant or benign). Such tissues may contain cells that are normal, pre-cancerous or cancerous, any combination of cells that are normal, pre-cancerous or cancerous, or any other form of diseased cell.

As will be readily appreciated, there are numerous methods well known in the art for determining whether cells are normal, pre-cancerous, cancerous or diseased, including histopathology and other phenotypic and genotypic methods of identifying cells.

The binding of the nucleic acid ligands to the pool of target molecules of the methods of the present invention may be performed under suitable conditions known in the art. For example, the concentrations of both ligand and target, buffer composition and temperature may be selected according to the specific parameters of the particular binding reaction.

In one embodiment, the concentration of the nucleic acid ligands is in the range of 5 ug/ml to 50 ug/ml. As will be appreciated the concentration of the pool of target molecules will depend on the particular details of the types of target and the constituent target molecules. In one specific embodiment, the concentration of the pool of target molecules is less than or equal to 20 mg/ml.

In one embodiment, the binding buffer includes a phosphate buffer and/or a Tris buffer. In one specific embodiment, the binding buffer includes 10 mM phosphate. The binding buffer may also include one or more salts to facilitate appropriate binding, including NaCl and/or $MgCl_2$. In one embodiment, the binding buffer contains 0.15 M NaCl and 5 mM $MgCl_2$. The temperature of binding may be selected with regard to the particular binding reaction. In one embodiment, the binding reaction is performed at a temperature in the range from 4° C. to 40° C. In one specific embodiment, the binding reaction is performed at a temperature in the range of 20° C. to 37° C.

The isolation of the nucleic acid ligands that bind to the pool of target molecules may be achieved by a suitable method that allows for unbound nucleic acid molecules to be separated from bound nucleic acids. For example, the pool of target molecules may be functionally coupled to a solid support and unbound nucleic acid molecules removed by washing the solid support under suitable conditions.

In the case where the pool of molecules is a pool of molecules isolated from a cell extract or a biological mixture of components, such as serum, the constituent proteins may be immobilised on an activated solid support. For the immobilisation of cell extracts, activated Sepharose beads are suitable for the immobilisation of proteins. Alternatively protein mixtures may be biotinylated, for example by reacting a biotin moiety with the free amino groups of lysine residues, and using streptavidin coupled to a solid support to capture the proteins.

The washing of nucleic acids not bound to the target pool of molecules may be performed in a suitable buffer under suitable conditions well known in the art; the washing being performed until a desired level of nucleic acid ligands remaining bound to target molecules is achieved. In one embodiment, unbound nucleic acids are removed from the pool of target molecules by washing multiple times in the buffer used for binding.

The bound nucleic acids may then be isolated from the pool of target molecules by a suitable method well known in the art, including the washing of the bound nucleic acid ligands by a buffer of sufficient stringency to remove the bound nucleic acids. Alternatively, for nucleic acid ligands bound to cellular extracts, bound nucleic acids may be isolated by extracting both the nucleic acid ligands and the nucleic acids of the cellular extract. For example, for nucleic acid ligands bound to cellular extracts, the nucleic acids may be isolated by guanidine thiocyanate extraction, followed by acid phenol treatment and ethanol precipitation. If the nucleic acid ligand is a ribonucleic acid, the nucleic acid may first be converted to a cDNA copy by reverse transcriptase. Alternatively, for tissue extracts such as formalin-fixed tissue extracts, the tissue extract may be digested with a proteinase (for example proteinase K) in the presence of a detergent (for example sodium dodecyl sulphate) and bound nucleic acid ligands isolated in this manner.

Amplification of the isolated (ie bound) nucleic acid ligands according to the methods of the present invention may be performed by a nucleic acid amplification process well known in the art. Examples of such amplification processes include polymerase chain reaction (PCR) using appropriately designed primers, rolling circle replication and/or cloning of the nucleic acid ligands into amplifiable vectors. In the case of PCR, both symmetric and asymmetric PCR may be used. For rolling circle replication, amplification using this method may occur from circularised nucleic acid ligands as templates, or alternatively, the pool of nucleic acid ligands may be cloned (after conversion to a double stranded intermediate by synthesis of the complementary strand) into a vector and rolling circle replication performed on double or single stranded template.

The reiteration of the steps of binding and isolation of nucleic acid ligands may be performed for any number of cycles required to achieve a desired level of binding specificity of one or more of the nucleic acid ligands to the pool of target molecules. The desired level of binding specificity may be determined by a method well known in the art, including determination of the proportion of nucleic acids bound to the target molecules using detectably labelled nucleic acid ligands.

As will be appreciated, one or more individual nucleic acid ligands may then be isolated from the final pool of nucleic acid ligands. The isolation of individual nucleic acid ligands may be achieved by a method well known in art, including the cloning of the pool of nucleic acid ligands into a suitable vector and the isolation of specific clones. The cloning of the final pool may or may not include a prior step of amplification to increase the number of targets for cloning. The DNA sequence of each cloned DNA, and therefore the sequence of the nucleic acid ligand, may be determined by standard procedures if so desired.

The specific nucleic acid ligand may then be regenerated by a process including PCR, excision of DNA from the cloning vector or in vitro transcription. In the case of methods of regenerating the nucleic acid ligand that involve a double stranded nucleic acid intermediate (ie PCR and cloning), the single stranded nucleic acid may be separated from its complementary nucleic acid by a method well known in the art, including denaturing electrophoresis, denaturing HPLC or labelling of one of the strands with a moiety (for example biotin) that allows separation of the strands by electrophoresis, basic pH induced strand separation, or HPLC.

The present invention also provides a method for isolating a pool of nucleic acid ligands capable of binding to one or more target molecules in a complex mixture, the method including the steps of:

(a) providing a pool of candidate nucleic acid ligands;
(b) providing a first pool of target molecules;
(c) providing a second pool of target molecules, wherein the second pool of target molecules may be isolated from the first pool of target molecules, and wherein the second pool of target molecules differs from the first pool of target molecules in that one or more of the target molecules in the second pool is present at a higher concentration than that present in the first pool of target molecules;
(d) allowing the nucleic acid ligands to bind to the first and second pools of target molecules, wherein the first and second pool of target molecules are in the presence of one another;
(e) isolating the nucleic acid ligands bound to the second pool of target molecules;
(f) amplifying the isolated nucleic acid ligands bound to the second pool of target molecules;

(g) reiterating steps (a) through (f) using the amplified nucleic acid ligands as the pool of candidate nucleic acid ligands, wherein the steps are reiterated until a final pool of nucleic acid ligands is obtained with a desired level of binding specificity to the second pool of target molecules; and (h) isolating the final pool of nucleic acid ligands so produced, wherein the final pool of nucleic acid ligands allows the differentiation of a test pool of molecules from a control pool of molecules.

In this embodiment, the present invention also provides a method for isolating a pool of nucleic acid ligands capable of binding to one or more target molecules in a complex mixture, wherein the pool of nucleic acid ligands allows the differentiation of a test pool from a control pool of molecules.

In one embodiment, the first pool of target molecules and the second pool of target molecules are both derived from cellular extracts. As such, the cellular extracts may include nucleic acids, proteins, oligosaccharides, small molecules and lipids. In one specific embodiment, the second pool of target molecules is derived from a population of cells phenotypically or genotypically similar to the population of cells from which the first pool of target molecules is derived.

The first pool of target molecules in one embodiment is a cellular extract, including a cellular extract derived from a tissue (eg chemically preserved tissue), including tissue sections and formalin fixed tissue sections. In one specific embodiment, the cellular extract is derived from human cells. Cellular extracts may be prepared by methods well known in the art.

In one embodiment, the first pool of target molecules is a cellular extract derived from cells selected from one or more of the following types of tissue: colorectal tissue, breast tissue, cervical tissue, uterine tissue, renal tissue, pancreatic tissue, esophageal tissue, stomach tissue, lung tissue, brain tissue, liver tissue, bladder tissue; bone tissue, prostate tissue, skin tissue, ovary tissue, testicular tissue, muscle tissue or vascular tissue. These tissues may contain cells that are normal (non-cancerous), pre-cancerous (having acquired some but not all of the cellular mutations required for a cancerous genotype), pathologically abnormal, or cancerous cells (malignant or benign). Such tissues may contain cells that are normal, pre-cancerous, pathologically abnormal or cancerous, any combination of cells that are normal, pre-cancerous, pathologically abnormal, or cancerous, or any other form of diseased cell.

In one specific embodiment, the first pool of target molecules is a cellular extract derived from normal or pre-cancerous cells.

The second pool of target molecules in one embodiment is a cellular extract, including a cellular extract derived from a tissue, including tissue sections and formalin fixed tissue sections. In one specific embodiment, the cellular extract is derived from human cells.

In one embodiment, the second pool of target molecules is a cellular extract derived from cells selected from one or more of the following types of tissue: colorectal tissue, breast tissue, cervical tissue, uterine tissue, renal tissue, pancreatic tissue, esophageal tissue, stomach tissue, lung tissue, brain tissue, liver tissue, bladder tissue, bone tissue, prostate tissue, skin tissue, ovary tissue, testicular tissue; muscle tissue or vascular tissue These tissues may contain cells that are normal (non-cancerous), pre-cancerous (having acquired some but not all of the cellular mutations required for a cancerous genotype), pathologically abnormal or cancerous cells (malignant or benign). Such tissues may contain cells that are normal, pre-cancerous, pathologically abnormal or cancerous, any combination of cells that are normal, pre-cancerous, pathologically abnormal, or cancerous, or any other form of diseased cells.

In one specific embodiment, the second pool of target molecules is a cellular extract derived from pre-cancerous, pathologically abnormal or cancerous cells.

The binding of the nucleic acid ligands to the first pool of target molecules in the presence of a second pool of target molecules may be performed under suitable conditions and in a suitable buffer. In one embodiment, the first pool of molecules will be in a molar excess to the second pool of molecules for the binding of the nucleic ligands. In one embodiment, the first pool of molecules will be in a ten fold or greater molar excess to the second pool of molecules for the binding of the nucleic ligands.

This embodiment of the present invention requires the ability of the nucleic acid ligands binding to the second pool of target molecules to be isolated from the first pool of target molecules. The isolation of the second pool of target molecules from the first pool of target molecules may be achieved by the spatial separation of the pools of targets on a solid support, so that the isolation of the second pool of molecules may be achieved by isolating that part of the solid support containing the second pool of target molecules. For example, in the case whereby fixed tissue sections containing, normal cells and a group of abnormal cells are used, the abnormal fixed cells will be physically separated from the normal fixed cells. Isolation of the second pool of target molecule with bound nucleic acid ligands may be accomplished by physically removing the portion of solid support having the second pool of target molecules bound to it.

Alternatively, the isolation of the second pool of target molecules from the first pool of nucleic acids may be achieved by a method that allows the separation of the first pool of target molecules from the second pool. For example, a first pool of normal cells may be isolated from a second pool of diseased cells by a method such as FACS (fluorescence activated cell sorting) or the capture of cells by antibodies to specific cell surface antigens. Alternatively, the different cells may be isolated by using a specific molecule that binds to a cell surface marker and which is attached to a solid support, such as a magnetic bead. Also, chemical coupling techniques may be used to couple a selectable moiety to the second pool of target molecules, and thereby allow isolation of the second pool of molecules from the first pool of target molecules. A further method of isolating cells is the use of laser capture microscopy.

The washing of the nucleic acids to remove nucleic acids not bound to the second pool of molecules may be achieved using a suitable buffer under suitable conditions. For the washing of nucleic acids bound to cellular extracts, the first pool of target molecules and the second pool of target molecules with bound nucleic acid ligands may or may not be washed together. In one embodiment, the washing involves washing multiple times in the original binding buffer as a means to remove unbound nucleic acid ligands.

The reiteration steps of this embodiment of the present invention are continued until the desired level of binding specificity to the second pool of target molecules is achieved. In one embodiment, the reiterations are continued until the proportion of the nucleic binding to the second pool of target molecules does not show any significant increase. The determination of the proportion of nucleic acid ligands binding to the second pool may be achieved by a method well known in the art, including detectably labelling a proportion of the nucleic acid ligands and determining the extent of binding. Detection of the nucleic acids ligands by a biotin:steptavidin method is a suitable method.

Alternatively, the steps may be reiterated until the pool of nucleic acid ligands shows specific binding to the target cell population and exhibits only a lower or background binding to other regions. Detection of the nucleic acids ligands by a biotin:steptavidin method is a suitable method.

The final pool of nucleic acid ligands so produced will allow the differentiation of a test pool of molecules from a control pool of molecules. The differentiation may be achieved by methods well known in the art including detectably labelling the final pool of nucleic acid ligands and determining the extent of binding to the test pool of molecules and the control pool of molecules. Detection of the nucleic acids ligands by a biotin:steptavidin method is a suitable method.

The test pool of target molecules in one embodiment is a cellular extract, including a cellular extract derived from a tissue, including tissue sections and formalin fixed tissue sections. In one specific embodiment, the cellular extract is derived from human cells.

In one embodiment, the test pool of target molecules is a cellular extract derived from cells selected from one or more of the following types of tissue: colorectal tissue, breast tissue, cervical tissue, uterine tissue, renal tissue, pancreatic tissue, esophageal tissue, stomach tissue, lung tissue, brain tissue, liver tissue, bladder tissue, bone tissue, prostate tissue, skin tissue, ovary tissue, testicular tissue, muscle tissue or vascular tissue. These tissues may contain cells that are normal (non-cancerous), pre-cancerous (having acquired some but not all of the cellular mutations required for a cancerous genotype), pathologically abnormal, or cancerous cells (malignant or benign). Such tissues may contain cells that are normal, pre-cancerous or cancerous, any combination of cells that are normal, pre-cancerous, pathologically abnormal or cancerous, or any other form of diseased cells.

In one specific embodiment, the test pool of target molecules is a cellular extract derived from pre-cancerous or cancerous cells. For example, the test pool of molecules is a cellular extract derived from cells that are the same, or genotypically or phenotypically similar, to the cells from which the cellular extract of the second pool of target molecules is derived.

The control pool of target molecules in one embodiment is a cellular extract, including a cellular extract derived from a tissue, including tissue sections and formalin fixed tissue sections. In one, specific embodiment, the cellular extract is derived from human cells.

In one embodiment, the control pool of target molecules is a cellular extract derived from cells selected from one or more of the following types of tissue: colorectal tissue, breast tissue, cervical tissue, uterine tissue, renal tissue, pancreatic tissue, esophageal tissue, stomach tissue, lung tissue, brain tissue, liver tissue, bladder tissue, bone tissue, prostate tissue, skin tissue, ovary tissue and testicular tissue. These tissues may contain cells that are normal (non-cancerous), pre-cancerous (having acquired some but not all of the cellular mutations required for a cancerous genotype), pathologically abnormal, or cancerous cells (malignant or benign). Such tissues may contain cells that are normal, pre-cancerous, pathologically abnormal or cancerous, any combination of cells that are normal, pre-cancerous, pathologically abnormal or cancerous, or any other form of diseased cells.

In one embodiment, the control pool of target molecules is a cellular extract derived from normal or pre-cancerous cells. In one specific embodiment, the control pool of molecules is a cellular extract derived from cells that are the same, or genotypically or phenotypically similar, to the cells from which the cellular extract of the first pool of target molecules is derived.

This embodiment of the present invention also contemplates the isolation of one or more individual nucleic acid ligands from the final pool, each of the nucleic acid ligands so isolated being capable of binding to a target molecule in a complex mixture, such as the complex mixture present in the second pool of target molecules or the complex mixture in the test pool of molecules.

Accordingly, in an another embodiment the present invention also provides a method for isolating a nucleic acid ligand capable of binding to a target molecule in a complex mixture, the method including the steps of:
  (a) providing a pool of candidate nucleic acid ligands;
  (b) providing a first pool of target molecules;
  (c) providing a second pool of target molecules, wherein the second pool of target molecules may be isolated from the first pool of target molecules, and wherein the second pool of target molecules differs from the first pool of target molecules in that one or more of the target molecules present in the second pool is present at a higher concentration than that present in the first pool of target molecules;
  (d) allowing the nucleic acid ligands to bind to the first and second pools of target molecules, wherein the first and second pool of target molecules are in the presence of one another;
  (e) isolating the nucleic acid ligands bound to the second pool of target molecules;
  (f) amplifying the isolated nucleic acid ligands bound to the second pool of target molecules;
  (g) reiterating steps (a) through (f) using the amplified nucleic acid ligands as the pool of candidate nucleic acid ligands, wherein the steps are reiterated until a final pool of nucleic acid ligands is obtained with a desired level of binding specificity to the second pool of target molecules;
  (h) isolating the final pool of nucleic acid ligands so produced, wherein the final pool of nucleic acid ligands allows the differentiation of a test pool of molecules from a control pool of molecules; and
  (i) isolating a nucleic acid ligand from the final pool of nucleic acid ligands, wherein the isolated nucleic acid ligand is capable of binding to a target molecule in a complex mixture.

In one embodiment, the nucleic acid ligand isolated (which is capable of binding to a target molecule in the complex mixture) allows the differentiation of a test pool of molecules from a control pool of molecules.

The present invention further provides a method for isolating a plurality of individual nucleic acid ligands capable of binding to a plurality of different target molecules in a complex mixture of molecules, the method including the steps of:
  (a) providing a pool of candidate nucleic acid ligands;
  (b) providing a pool of target molecules, wherein the target molecules in the pool may be isolated;
  (c) allowing the nucleic acid ligands to bind to the target molecules;
  (d) isolating the nucleic acid ligands bound to the pool of target molecules;
  (e) amplifying the isolated nucleic acid ligands;
  (f) isolating an individual nucleic acid ligand from the amplified nucleic acid ligands;
  (g) using the individual nucleic acid ligand to deplete the pool of target molecules of a specific molecule;

(h) reiterating steps (a) to (g) using the successively depleted pool of target molecules as the starting pool of target molecules for each cycle of reiteration, wherein the steps are reiterated until a plurality of individual nucleic acid ligands is identified.

In this embodiment the present invention provides a method for the isolation of a plurality of individual nucleic acids capable of binding to a plurality of specific molecules in a complex mixture of molecules. The ability to isolate a plurality of individual nucleics may be useful, for example, for monitoring the extent of expression of a number of molecules simultaneously in a complex mixture.

As will be appreciated, in this embodiment a nucleic acid ligand is isolated from a pool of nucleic acid ligands that binds to a complex mixture and the nucleic acid ligand so isolated is then used to deplete the complex mixture of the specific target molecule that binds the ligand. The process is then reiterated until a plurality of nucleic acid ligands capable of binding to a plurality of specific molecules is achieved. Accordingly, the present invention further contemplates one or more individual nucleic acid ligands isolated from the plurality of nucleic acid ligands isolated by this method.

To deplete the pool of target molecules, an individual nucleic acid ligand may be produced in large quantities and coupled to a solid support. Chemical synthesis methods (if the nucleotide sequence of the ligand has been determined), PCR amplification or in vitro transcription (for RNA nucleic acid ligands) are suitable methods for producing quantities of the nucleic acid ligand suitable for coupling to the solid support.

The depletion of the specific molecule from the pool of target molecules may be achieved by passing the pool of target molecules over the nucleic acid ligand bound to the solid support and retaining the eluate. For example, biotinylated oligonucleotides may be used as the nucleic acid ligand, and the depletion of the specific molecule from the pool of target molecules may be achieved by allowing the specific molecule to bind to an excess of the oligonucleotide, and then isolating the nucleic acid-protein complex by binding the oligonucleotide to streptavidin paramagnetic beads.

The remaining eluate is then to be used in the next round of binding as the pool of target molecules. In this manner the eluate becomes successively depleted in specific molecules, and specifically enriched for those molecules to which a nucleic acid ligand has not been identified.

The process may then be reiterated to isolate new nucleic acid ligands to one or more of the remaining targets molecules in the depleted pool of targets using a fresh candidate pool of nucleic acid ligands for each round. Alternatively, the pool of nucleic acid ligands that bound to the pool of target molecules may be used as the candidate pool of nucleic acid ligands. In this case, it may be necessary to further amplify this pool of nucleic acid ligands so as to attain a concentration of nucleic acid ligands that may be used as the starting pool of candidate nucleic acid ligands.

As will be appreciated, multiple nucleic acid ligands may also be used at each cycle of reiteration to accelerate the identification of nucleic acid ligands.

Reiteration of the process allows the isolation of a plurality of individual nucleic acid ligands capable of binding to a plurality of specific molecules in a complex mixture of molecules. Eventually, such a process should yield a nucleic acid ligand for every molecule in a complex pool of targets.

The identification of a plurality of individual nucleic acid ligands capable of binding to a plurality of specific molecules in a complex mixture of molecules may then be used to determine the individual concentration of each specific molecule so identified in the complex.

In one embodiment, the plurality of individual nucleic acid ligands can be used to determine the concentration of a plurality of specific molecules in a target complex by using each individual nucleic acid as a separate ligand in a quantifiable system. For example, the quantifiable system may consist of a system in which the individual nucleic acid ligand is coupled to a solid support and the concentration of the specific molecule is determined by a competitive binding assay procedures known in the art. Diagnostic applications of the method of the present invention may then be envisaged.

As will be appreciated, the identity of the specific molecule to which the isolated individual nucleic acid ligands binds may also be determined if so desired. This may be achieved by methods well known in the art, including coupling a suitable amount of the single stranded DNA to a solid support and purifying the target molecule by affinity chromatography. Once the target molecule has been substantially purified, the identity of the molecule may be determined by a suitable means. Mass spectrometry methods for determining the identity of the specific molecule are suitable.

The present invention also provides a polynucleotide including the nucleotide sequence according to SEQ ID No. 1.

In this embodiment of the present invention, a polynucleotide with the following sequence is provided:

```
SEQ ID NO: 1:
5'GGGAGCTCAGAATAAACGCTCAAGGAACAGCAAGATACGGTCACCGAA
CATAGCGCACCACAGGCACA3'.
```

This nucleotide sequence is the sequence of a nucleic acid ligand capable of distinguishing malignant mesothelioma cells from non malignant mesothelial cells. Preliminary data also suggests that this nucleic acid ligand may also be capable of distinguishing malignant and non-malignant colon cells, and malignant and non-malignant prostate cells.

The polynucleotide according to the various embodiments of the present invention may be modified at one or more base moieties, sugar moieties, or the phosphate backbone, and may also include other appending groups to facilitate the function of the polynucleotide to function as a nucleic acid ligand or as a diagnostic reagent.

For example, the polynucleotide may include at least one modified base moiety, such as 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The polynucleotide may also include at least one modified sugar moiety such as arabinose, 2-fluoroarabinose, xylulose, and hexose.

The polynucleotide may be synthesized, purified and isolated by a method known in the art. For example, phosphorothioate polynucleotides may be synthesized by the method as described in Stein et al. (1988) Nucl. Acids Res. 16: 3209. Alternatively, the polynucleotide may be synthesized as a double stranded DNA by an amplification reaction such as PCR from a DNA template, and the complementary strand removed by either isolating the single strand with the polynucleotide or by digesting the complementary strand (phosphorylated at its 5' end) with an enzyme such as lambda exonuclease.

The polynucleotide may consist only of the nucleotide sequence of SEQ ID NO:1, or alternatively, may further include one or more flanking nucleotide sequences. For example, the polynucleotide may include one or more flanking sequences that are used to amplify the polynucleotide sequence, and/or 5' and 3' capping structures known in the art to provide further stability to the polynucleotide in vitro or in vivo.

Studies have indicated that a polynucleotide including SEQ ID No.1 may be useful as diagnostic reagent for identifying at least one difference at the molecular level between malignant and non-malignant cells. In particular, the polynucleotide is capable of identifying at least one difference at the molecular level between malignant mesothelioma cells (including epithelioid mesothelioma cells, biphasic mesothelioma cells, desmoplastic mesothelioma cells and sarcomatoid mesothelioma cells) and non-malignant mesothelial cells (including benign or reactive mesothelial cells); and may be capable of identifying at least one difference at the molecular level between malignant prostate cells and non-malignant prostate cells, and malignant colon cells and non-malignant colon cells.

The polynucleotide of the various embodiments of the present invention may be routinely adapted for diagnostic purposes as a nucleic acid ligand according to any number of techniques employed by those skilled in the art. The nucleic acid ligand may be labelled by procedures known in the art in order to track the presence of the ligand. For example, the nucleic acid ligand may be labelled with biotin and the nucleic acid ligand detected by way of a biotin:streptavidin complex.

The present invention also provides a polynucleotide including a variant of the nucleotide sequence according to SEQ ID NO.1, wherein the polynucleotide forms a nucleic acid ligand that identifies at least one difference at the molecular level between two complex biological mixtures.

In this regard, the term "complex biological mixture" as used throughout the specification is to be understood to mean a collection of two or more different target molecules derived from a biological source. For example, the complex biological mixture may be a cellular extract derived from a cell (such as a cell present in a formalin fixed tissue, or an extract of molecules from one or more cells such as blood plasma). The complex biological mixture may also be an isolated cell (such as cell in tissue culture or a cell isolated from a biological source, such as a cell isolated by FACS), the complex biological mixture may be one or more cells present in a tissue sample, a biological fluid (such as blood) or in a biopsy, or the complex biological mixture one or more cells present in an entire human or animal.

In addition, the term "variant" as used throughout the specification will be understood to mean any DNA or RNA polynucleotide that is a fragment of a specific nucleotide sequence, or any DNA or RNA polynucleotide that contains one or more base substitutions, deletions or insertions of the specific nucleotide sequence or a fragment of this polynucleotide. The variant will be capable of forming a nucleic acid ligand that identifies at least one difference at the molecular level between two complex biological systems and has the ability to competitively inhibit the binding of specific nucleotide sequence to its target.

In this regard, it will be appreciated that the polynucleotide sequence according to SEQ ID NO:2 (aptamer MTA R720) is a possible variant of SEQ ID NO:1 (aptamer MTA R72).

SEQ ID NO: 2:
5'GGGAGCTCAGAATAAACGCTCAACAAAAGACTATCCAGCGACACGCAA

TCTCAAGCAACAGAGGACAG3'

In the case where the variant is a fragment of SEQ ID NO:1, the fragment may be any DNA or RNA polynucleotide. A nucleotide sequence including one or more base substitutions, deletions or insertions of the nucleotide sequence according to SEQ ID NO:1 is any DNA or RNA polynucleotide that contains one or more base substitutions, deletions or insertions of the nucleotide sequence of SEQ ID NO:1, or a fragment thereof. Such variants will also be capable of forming a nucleic acid ligand that identifies at least one difference at the molecular level between two complex biological mixtures.

In one embodiment, the polynucleotide forms a nucleic acid ligand that identifies at least one difference at the molecular level between malignant and non-malignant cells. In one specific embodiment, the polynucleotide forms a nucleic acid ligand that identifies at least one difference at the molecular level between malignant and non-malignant cells present in a chemically preserved tissues, such as formalin fixed tissue sample.

In one embodiment, the polynucleotide forms a nucleic acid ligand that identifies at least one difference at the molecular level between the following malignant and non-malignant cells:

(i) malignant mesothelioma cells (including epithelioid mesothelioma cells, biphasic mesothelioma cells, desmoplastic mesothelioma cells and sarcomatoid mesothelioma cells) and normal lung cells or benign or reactive mesothelial cells;
(ii) malignant colon cells and non-malignant colon cells;
(iii) malignant prostate cells and non-malignant prostate cells.

The ability of the polynucleotide to form a nucleic acid ligand that identifies at least one difference at the molecular level between two complex biological mixtures may be confirmed by exposing the nucleic acid ligand under the appropriate conditions to each of the complex biological mixtures and detecting the extent of differential binding of the nucleic acid ligand to the mixtures.

For example, for distinguishing between malignant mesothelioma cells and non-malignant mesothelial cells, formalin fixed tissue sections may be used. In this case, the sections may be de-paraffinised and washed through a series of graded alcohol before undergoing antigen retrieval (121° C. in sodium citrate buffer pH 6.5 for 12 min, then left to cool for 2 hrs). The antigen retrieved tissue sections may then be equilibrated in binding buffer (1×PBS, 5 mM $MgCl_2$) and incubated overnight in a humidified chamber with thermally equilibrated nucleic acid ligand (1-10 nM). The sections may then be thoroughly washed in binding buffer to remove unbound ligand and the bound ligand detected. An Enzyme Labelled Fluorescence (ELF) kit (Molecular Probes, USA) is suitable for this purpose. In this instance, the biotinylated ligand is bound to streptavidin which is bound to alkaline phosphatase that reacts with the ELF substrate. This reaction produces an intensely fluorescent yellow green precipitate at the site of enzymatic activity.

A similar procedure is also suitable for distinguishing malignant colon cells from non-malignant colon cells, and malignant prostate cells from non-malignant prostate cells.

In the case of a variant which is a base substitution, insertion and/or deletion of SEQ ID NO:1, in one embodiment the variant polynucleotide includes 5 or less base changes from the primary sequence of SEQ ID NO:1. In one specific embodiment, the variant includes 3 or less base changes from the primary sequence of SEQ ID NO:1, and in a further embodiment, includes 1 base change from the primary sequence of SEQ ID NO:1.

In one embodiment, the variant has at least 80% sequence identity with SEQ ID NO:1. In one specific embodiment, the variant has at least 90% sequence identity with SEQ ID NO:1. In a further embodiment, the variant has at least 95% sequence identity with SEQ ID NO:1, for example at least 98% sequence identity with SEQ ID NO:1.

Various algorithms known in the art exist for determining the degree of homology between any two nucleic acid sequences. For example, the BLAST algorithm can be used for determining the extent of sequence homology between two sequences. BLAST identifies local alignments between two sequences and predicts the probability of the local alignment occurring by chance. The BLAST algorithm is as described in Altschul et al., 1990, J. Mol. Biol. 215:403-410.

A fragment of SEQ ID NO:1 may be synthesized, purified and isolated by a method known in the art. For example, phosphorothioate polynucleotides may be synthesized by the method as described in Stein et al. (1988) Nucl. Acids Res. 16: 3209. Alternatively, the fragment may be synthesized as a double stranded DNA by an amplification reaction such as PCR from a DNA template, and the complementary strand removed by either isolating the single strand with the polynucleotide according to SEQ ID NO:1, or by digesting the complementary strand (phosphorylated at its 5' end) with an enzyme such as lambda exonuclease.

In the case of the variant being a base substitution, deletion or insertion, the polynucleotide may also synthesized in vitro, with the appropriate substitution, deletion or insertion being incorporated during the synthesis reaction. Alternatively, a clone having the cloned aptamer sequence may be mutagenised to incorporate a base substitution, deletion or insertion by a method known in the art.

The present invention also provides a polynucleotide sequence that hybridises with the complement of SEQ ID NO.1 under stringent hybridisation conditions, wherein the polynucleotide forms a nucleic acid ligand that identifies at least one difference at the molecular level between two complex biological mixtures.

In this regard, the term "hybridises" or "hybridisation" (or variants thereof) is to be understood to mean any process by which a strand of nucleic acid binds with a complementary strand through base pairing. Hybridisation may occur in solution, or between one nucleic, acid sequence present in solution and another nucleic acid sequence immobilized on a solid support (e.g., membranes, filters, chips etc).

In addition, the term "stringent conditions" is to be understood to mean the conditions that allow complementary nucleic acids to bind to each other within a range from at or near the Tm (Tm is the melting temperature) to about 20° C. below Tm. Factors such as the length of the complementary regions, type and composition of the nucleic acids (DNA, RNA, base composition), and the concentration of the salts and other components (e.g. the presence or absence of formamide, dextran sulphate and/or polyethylene glycol) must all be considered, essentially as described in Current Protocols in Molecular Biology, John Wiley & Sons, N.Y. (1989).

An example of stringent conditions is hybridisation at 4×SSC at 65° C., followed by a washing in 0.1×SSC at 65° C. for one hour.

For example, the polynucleotide with a nucleotide sequence which is the complement of SEQ ID NO:1 may be immobilised on a filter, as described in Sambrook, J, Fritsch, E. F. and Maniatis, T. Molecular Cloning: A Laboratory Manual 2nd. ed. Cold Spring Harbor Laboratory Press, New York. (1989). To determine if the polynucleotide of interest hybridises to the complement of SEQ ID NO:1, the conditions allowing hybridisation under stringent conditions: prehybridization may be performed in a prehybridization solution (eg 4×SSC (1×=100 mM NaCl, 10 mM sodium citrate, pH 7.0), 5×Denhardt's reagent (1 g/l each of Ficoll, Polyvinyl-pyrrolidone, Bovine Serum Albumin), 1.0% SDS, 100 ug/ml denatured, fragmented salmon sperm DNA) for 2 to 12 hours. Hybridization of the probe with the target (ie filter) may then be performed under conditions such as 4×SSC, 1.0% SDS, 100 ug/ml denatured, fragmented salmon sperm DNA, at 65° C. overnight. The filter may then be washed with 0.1×SSC and 0.1% SDS at room temperature for 15 min at 20° C.

Accordingly, in another embodiment the present invention provides a polynucleotide which hybridises with the complement of the nucleotide sequence according to SEQ ID NO.1 under stringent hybridisation conditions, wherein the polynucleotide is capable of forming a nucleic acid ligand that identifies at least one difference at the molecular level between two complex biological mixtures, and wherein the stringent hybridisation conditions include hybridisation in 4×SSC at 65° C. and washing in 0.1×SSC at 65° C.

Another example of stringent conditions is hybridisation at 42° C. in a solution including 50% formamimide, 5×SSC and 1% SDS or at 65° C. in a solution including 5×SSC and 1% SDS, with a wash in 0.2×SSC and 0.1% SDS at 65° C.

Accordingly, in another embodiment the present invention provides a polynucleotide sequence which hybridises with the complement of SEQ ID NO.1 under stringent hybridisation conditions, wherein the polynucleotide is capable of forming a nucleic acid ligand that identifies at least one difference at the molecular level between two complex biological mixtures, and wherein the stringent hybridisation conditions include hybridisation in 50% formamide, 5×SSC and 1% SDS at 65° C. and washing in 0.2×SSC and 0.1% SDS at 65° C.

As described previously, the ability of the polynucleotide to form a nucleic acid ligand that identifies at least one difference at the molecular level between two complex biological mixtures may be confirmed by exposing the nucleic acid ligand under the appropriate conditions to each of two complex biological mixtures and detecting the extent of differential binding of the nucleic acid ligand to the mixtures.

As described previously, the polynucleotide may be synthesized, purified and isolated by a method known in the art. For example, phosphorothioate polynucleotides may be synthesized by the method as described in Stein et al. (1988) Nucl. Acids Res. 16: 3209.

The present invention also provides a nucleic acid ligand that has the ability to distinguish a Malignant cell from a non-malignant cell.

Nucleic acid ligands as described herein may be useful for distinguishing malignant mesothelioma cells (including epithelioid mesothelioma cells, biphasic mesothelioma cells, desmoplastic mesothelioma cells and sarcomatoid mesothelioma cells) from non-malignant mesothelial cells or benign or reactive mesothelial cells.

As such, the present invention contemplates the following further embodiments of the present invention:

(i) A polynucleotide including the nucleotide sequences according to SEQ ID NO:1;

(ii) A polynucleotide including a variant of the nucleotide sequence according to SEQ ID NO.1, wherein the polynucleotide forms a nucleic acid ligand that identifies at least one difference at the molecular level between two complex biological mixtures. In this regard, the polynucleotide forms a nucleic acid ligand that identifies at least one difference at the molecular level between a malignant mesothelioma cell and a non-malignant mesothelial cell;

(iii) A polynucleotide that hybridises with the complement of the nucleotide sequence according to SEQ ID NO.1 under stringent hybridisation conditions, wherein the polynucleotide forms a nucleic acid ligand that identifies at least one difference at the molecular level between two complex biological mixtures. In this regard, stringent hybridisation conditions include hybridisation in 4×SSC at 65° C. and washing in 0.1×SSC at 65° C. or hybridisation in 50% formamide, 5×SSC and 1% SDS at 65° C. and washing in 0.2×SSC and 0.1% SDS at 65° C.;

(iv) A nucleic acid ligand including a nucleotide sequence according to SEQ ID NO:1, wherein the ligand distinguishes a malignant mesothelioma cell and the non-malignant cell from a non-malignant mesothelial cell;

(v) A method of identifying at least one difference at the molecular level between a first complex biological mixture and a second complex biological mixture, the method including the steps of:
(a) binding to a first complex biological mixture a nucleic acid ligand including the nucleotide sequence of SEQ ID NO:1, or a variant thereof;
(b) binding to a second complex biological mixture a nucleic acid ligand including the nucleotide sequence of SEQ ID NO:1, or a variant thereof; and
(c) identifying at least one difference at the molecular level between the first complex biological mixture and the second complex biological mixture by the differential binding of the nucleic acid ligand to the first complex biological mixture and the second biological mixture; and (vi) A method of identifying a malignant mesothelioma cell, the method including the steps of:
(a) binding to a test cell or cellular extract a nucleic acid ligand including the nucleotide sequence of SEQ. ID NO:1, or a variant thereof;
(b) binding to a non-malignant mesothelial cell or cellular extract a nucleic acid ligand including the nucleotide sequence of SEQ ID NO:1, or a variant thereof; and
(c) identifying the test cell as a malignant mesothelioma cell by differential binding of the nucleic acid ligand to the test cell or cellular extract and the non-malignant cell or cellular extract.

With regard to the nucleic acid ligand including the nucleotide sequence of SEQ ID NO:1, examples of malignant cells that may be distinguished by this nucleic acid ligand from non-malignant cells include malignant mesothelioma cells (including epithelioid mesothelioma cells, biphasic mesothelioma cells, desmoplastic mesothelioma cells and sarcomatoid mesothelioma cells) and normal lung cells or benign or reactive mesothelial cells.

The ability of the nucleic acid ligand to distinguish between a malignant cell and a non-malignant cell may be confirmed by exposing the nucleic acid ligand under the appropriate conditions to one or more malignant and non-malignant cells and detecting the extent of differential binding of the nucleic acid ligand to the malignant and non-malignant cells.

For example, for distinguishing between malignant mesothelioma cells and non-malignant mesothelial cells, formalin fixed tissue sections may be used. In this case, the sections may be de-paraffinised and washed through a series of graded alcohol before undergoing antigen retrieval (121° C. in sodium citrate buffer pH 6.5 for 12 min, then left to cool for 2 hrs). The antigen retrieved tissue sections may then be equilibrated in binding buffer (1×PBS, 5 mM $MgCl_2$) and incubated overnight in a humidified chamber with thermally equilibrated nucleic acid ligand (1-10 nM). The sections may then be thoroughly washed in binding buffer to remove unbound ligand and the bound ligand detected. An Enzyme Labelled Fluorescence (ELF) kit (Molecular Probes, USA) is suitable for this purpose. In this instance, the biotinylated ligand is bound to streptavidin which is bound to alkaline phosphatase that reacts with the ELF substrate. This reaction produces an intensely fluorescent yellow green precipitate at the site of enzymatic activity.

Accordingly, in another embodiment the present invention provides a nucleic acid ligand that distinguishes a malignant mesothelioma cell from a non-malignant mesothelial cell.

A similar procedure is also suitable for distinguishing malignant prostate or colon cells from non-malignant prostate or colon cells.

As described previously, the nucleic acid ligand may be synthesized, purified and isolated by a method known in the art. For example, phosphorothioate polynucleotides may be synthesized by the method as described in Stein et al. (1988) *Nucl. Acids Res.* 16: 3209.

The present invention also provides a method of identifying at least one difference at the molecular level between a first complex biological mixture and a second complex biological mixture, the method including the steps of:
(a) binding to a first complex biological mixture a nucleic acid ligand including the nucleotide sequence of SEQ ID NO:1 or a variant thereof;
(b) binding to a second complex biological mixture a nucleic acid ligand including the nucleotide sequence of SEQ ID NO:1 or a variant thereof; and
(c) identifying at least one difference at the molecular level between the first complex biological mixture and the second complex biological mixture by the differential binding of the nucleic acid ligand to the first complex biological mixture and the second biological mixture.

In one embodiment, the first complex biological mixture is a first cell or an extract thereof, and the second biological system is a second cell or an extract thereof.

The first and second cells may be present in a tissue sample such as a formalin fixed tissue sample, a biopsy or a blood sample. Alternatively, the first and second cells may be present as cells maintained or propagated in culture, or may be cells present in an entire animal or human.

In one embodiment, the first complex biological mixture is a cell in a formalin fixed tissue sample and the second complex biological mixture is a cell in a formalin fixed tissue sample.

In one embodiment, the first complex biological mixture is a malignant cell or an extract thereof, and the second cell is a non-malignant cell or an extract thereof. For example, the malignant cell may be a malignant mesothelioma cell (including an epithelioid mesothelioma cell, a biphasic mesothelioma cell, a desmoplastic mesothelioma cell or a sarcomatoid mesothelioma cell) and the non-malignant cell be a normal, benign or reactive mesothelial cell. Accordingly, in another embodiment the present invention provides a method of identifying a malignant mesothelial cell, the method including the steps of:
(a) binding to a test cell or cellular extract a nucleic acid ligand including the nucleotide sequence of SEQ ID NO:1 or a variant thereof;
(b) binding to a non-malignant mesothelial cell or cellular extract a nucleic acid ligand including the nucleotide sequence of SEQ ID NO:1 or a variant thereof; and
(c) identifying the test cell as a malignant mesothelial cell by differential binding of the nucleic acid ligand to the test cell or cellular extract and the non-malignant mesothelial cell or cellular extract.

The binding of the nucleic acid ligand to the first and second cells or cellular extracts may be performed under conditions suitable known in the art to allow the nucleic acid ligand to detect at least one difference between the cells.

For example, for distinguishing between malignant mesothelioma cells and non-malignant mesothelial cells, formalin fixed tissue sections may be used. In this case, the sections may be de-paraffinised and washed through a series of graded alcohol before undergoing antigen retrieval (121° C. in sodium citrate buffer pH 6.5 for 12 min, then left to cool for 2 hrs). The antigen retrieved tissue sections may then be equilibrated in binding buffer (1×PBS, 5 mM $MgCl_2$) and incubated overnight in a humidified chamber with thermally equilibrated nucleic acid ligand (1-10 nM). The sections may then be thoroughly washed in binding buffer to remove unbound ligand and the ligand detected. An Enzyme Labelled Fluorescence (ELF) kit (Molecular Probes, USA) is suitable for this purpose. In this instance, the biotinylated ligand is bound to streptavidin which is bound to alkaline phosphatase that reacts with the ELF substrate. This reaction produces an intensely fluorescent yellow green precipitate at the site of enzymatic activity.

A similar procedure is also suitable for distinguishing malignant prostate or colon cells from non-malignant prostate or colon cells.

As discussed previously, the nucleic acid ligand may be detectably labelled by a method known in the art. For example, the nucleic acid ligand may be labelled with biotin and the ligand detected by way of a biotin:streptavidin complex.

The present invention further contemplates the use of the various nucleic acid ligands as diagnostic agents, as therapeutic agents, or as carriers for therapeutic agents, for the treatment of various diseases, conditions and states. The present invention also contemplates the use of the various nucleic acid ligands as reagents for imaging for diagnostic purposes.

The present invention also contemplates the use of the nucleic acid ligands as tools for identification of their target molecules in complex mixtures. For example, by the use of affinity chromatography it may be possible to identify the various protein and non-protein targets of the ligands in cells.

In one embodiment, the present invention provides a method of identifying a target molecule associated with a mesothelioma cell and/or associated with mesothelioma tissue, the method including identifying a target molecule that binds a nucleotide sequence including SEQ ID NO:1.

The present invention also contemplates the use of the nucleic acid ligands as tools for the identification and/or isolation of various cell types, such as stem cells, fetal erythrocytes, trophoblasts and other rare or difficult to identify/isolate cell types. For example, the ligands may be labelled so as to allow FACS analysis of various cell types.

It will also be appreciated that in the various embodiments of the present invention in order to assist the isolation of aptamers that distinguish between two different complex mixtures, a competitive blocking step may be used.

In this step, a pool of aptamers is produced that bind to targets in complex mixture 1. This pool (pool 1,2) has sequences at the 5' and 3' end that allow amplification with primers 1 and 2. A second complex mixture is then screened with an aptamer library that can only be amplified with primers 3 and 4 in the presence of an excess of pool 1,2 (eg 5-10 fold molar excess). Unbound aptamers are washed away and bound aptamers recovered and amplified with primers 3 and 4. Any targets in complex mixture 2 that are also present in complex mixture 1 should be bound by aptamers in pool 1,2 and therefore unavailable for binding to aptamers in pool 3,4.

DESCRIPTION OF SPECIFIC EMBODIMENTS

The present invention will now be described in relation to various examples of specific embodiments. However, it must be appreciated that the following description is not to limit the generality of the above description.

Example 1

Isolation of a Pool of Nucleic Acid Ligands Capable of Differentiating Between Normal Liver Tissue and Cancerous Tissue Formalin fixed human tissue sections of colon tumour metastases in liver were prepared. Colon tumour metastases were identified in the liver tissue by standard histopathological procedures. A tissue section in which the tumourigenic tissue represented less than 10% of the total cell population in each section was selected.

A 5 micron thick tissue section was deposited on a glass slide and antigen retrieval performed by microwave irradiation.

One to fifty micrograms of a chemically synthesised aptamer library of average size of 85 nucleotides containing 45 bases of random sequence in 0.2 ml binding buffer (0.15 M NaCl, 10 mM phosphate pH 7.4, 5 mM $MgCl_2$) was used. The tissue section was washed six times with five millilitres of binding buffer to remove unbound aptamers. The tissue was viewed under a microscope where the tumourigenic target cell population was recovered by scraping with a scalpel or fine needle. Total nucleic acids were isolated from the scraped portion by proteinase K digestion in the presence of sodium dodecyl sulfate.

Recovered aptamers were then subject to PCR amplification using oligonucleotide primers to the defined 5' and 3' flanking regions. One primer was biotinylated to facilitate strand separation.

Amplified products were pooled, ethanol precipitated and then incubated with streptavidin Sepharose beads in order to bind the biotinylated DNA. The non-biotinylated strand was eluted from the beads using 0.1 M NaOH and then neutralised with 0.1M HCl. Eluted species were quantitated by gel electrophoresis using SYBr Gold stain on a Fluorimager. If the aptamer library used was RNA-based then the RNA aptamers were first converted to cDNA with reverse transcriptase using standard protocols before amplification. To regenerate RNA ligands for re-binding to the target, in vitro transcription was utilised from the amplified pool. Alternatively, the amplified products was cloned into a vector and the library of inserts then transcribed in vitro to regenerate the RNA ligands.

At this point the aptamer library was rebound to similar tissue sections and the process described above repeated. Cycles of the process were repeated until the yield of aptamer recovered from the tissue plateaued and or sequence analysis of randomly chosen aptamers from the selected pool revealed multiple examples of the same sequence.

The double stranded amplified DNA resulting from the final round of selection was cloned into a plasmid vector (for example pGEM T Easy from Promega) using *E. coli* DH5α as a hosts. The total plasmid DNA was isolated and the library of inserts amplified by PCR using one biotinylated primer and a normal primer. The resulting biotinylated strands were used to verify by staining of tissue sections that the pool of aptamers so isolated showed an increased signal to the tumourigenic tissue over the normal tissue in the sample.

This was done by incubating the biotinylated aptamer or aptamer pool at, a concentration of 1-20 nM with a new tissue section under exactly the same conditions that were used during screening Unbound aptamer was washed from the section and the sites of aptamer binding visualized using a streptavidin-horseradish peroxidase complex and a standard enzyme substrate.

Additional rounds of selection to remove nonspecific binding aptamers from the pool can be undertaken using sections from other non-target tissues.

Affinity of the aptamer population and/or individual aptamers can be further enhanced by performing mutagenesis on the selected aptamer pool followed by selection on target tissue sections as described.

Example 2

Isolation of a Pool of Individual Aptamers that Bind to Specific Molecules Present in Serum Serum proteins were concentrated by ammonium sulfate precipitation. The redissolved protein mixture was desalted by dialysis. Proteins were then immobilized on activated CH-Sepharose (Pharmacia) using conditions recommended by the supplier. Populations of beads were created with protein content varying between 1 and 25 microgram of protein per milligram of beads.

Alternatively the protein mixture was biotinylated with EZ-Link-sulfo-NH S-LC-Biotin (Pierce) which primarily reacts with free amino groups.

10-50 micrograms of single stranded DNA aptamer library ($>1 \times 10^{14}$ molecules) was thermally equilibrated in binding buffer then added to underivatized CH-Sepharose to remove Sepharose binding species. The mixture was incubated at room temperature for 1.5 hours with constant agitation.

Unbound aptamers in the bead supernatant were recovered by centrifugation and then added to protein coupled CH-Sepharose. The mixture was incubated at room temperature for 1.5 hours with constant agitation.

Protein coupled beads were washed 4 times in binding buffer and bound aptamers eluted in 7M urea with heating and recovered by ethanol precipitation. Recovered aptamers were then subject to PCR amplification using oligonucleotide primers to the defined-flanking regions. One primer was biotinylated to facilitate strand separation.

Amplified products were pooled, ethanol precipitated and then incubated with streptavidin Sepharose beads in order to bind the biotinylated DNA. The non-biotinylated strand was eluted from the beads using 0.1M NaOH and then neutralised with 0.1M HCl. Eluted species were quantitated by gel electrophoresis using SYBr Gold stain on a Fluorimager.

The aptamer population resulting from successive rounds of selection was cloned into a vector pGEM-T Easy (Promega) and individual clones isolated and sequenced. The inserts from each, of these clones was amplified by PCR using one oligonucleotide phosphorylated at the 5' end and one oligonucleotide with a biotin at the 5' end. The DNA strand containing the phosphorylated 5' end was degraded by incubating the PCR product with lambda exonuclease under standard conditions. The remaining single DNA strand, corresponding to the original aptamer sequence, was purified by standard phenol/chloroform extraction and ethanol precipitation.

An aliquot of the protein target mixture was then incubated with each biotinylated aptamer. The aptamer protein complex was then isolated from solution by binding to streptavidin Sepharose beads. Beads were washed several times with binding buffer and specifically bound proteins eluted from the immobilized aptamer using binding buffer containing 6M urea or 0.5% sodium dodecylsulfate. An aliquot of this eluate was then analyzed by SDS gel electrophoresis. In some cases further analysis by MALDI-TOF mass spectrometry using a Bruker Autoflex instrument was performed.

Each aptamer was then classified according to its binding specificity and nucleic acid sequence.

Aptamers shown to bind a single protein were then produced in large quantity either by solid phase synthesis or by PCR as described above and immobilized on a solid support as described.

The original target protein mixture was then passed over this population of aptamers to remove, proteins identified in the first round of selection.

Proteins which did not bind to these aptamers were then used for the second round of aptamer selection and protein identification. Repeated rounds of aptamer selection and protein identification will eventually allow isolation of an aptamer to and identification of every protein in the mixture.

Aptamers produced in this manner may then be incorporated into a diagnostic format that will allow the concentration of every protein in the target mixture to be determined. In addition the aptamers could be used to tag individual proteins for therapeutic or diagnostic purposes.

Example 3

Preparation of Aptamer Library

An 85 mer with a 45 base section of random nucleotide sequence was synthesized. The nucleotide sequence of the 85 mer is as follows:

(SEQ ID NO. 3)
5'-AGCTCAGAATAAACGCTCAANNNNNNNNNNNNNNNNNNNNNNNNNNNN

NNNNNNNNNNNNNNNNNNNNNTTCGACATGAGGCCCGGATC-3'

The 85 mer was dissolved in water to a concentration of approximately 100 μM.

To generate a biotin labelled aptamer for use in screening, an oligonucleotide with the following sequence was synthesized:

5'-GATCCGGGCCTCATGTCGAA-3' (SEQ ID NO. 4)

This oligonucleotide was dissolved in water to a concentration of 100 μM.

To anneal the oligonucleotide to the 85 mer, 25 µl of 100 µM 85-mer was mixed with 10 µl of 100 µM oligonucleotide, 30 µl Sequenase buffer (USB; 5×) and 94 water. The reaction was mixed and incubated at 68° C. for 5 minutes, the mix cooled to room temperature for 5 minutes.

To the above mix was added 16.5 µl 0.1 M DTT, 12.5 µl 10 mM dNTPs, 1 µl Sequenase (USB, 13 U/µl), 20 µl 5× Sequenase buffer and 41 µl $H_2O$. The reaction was incubated at 42° C. for 30 minutes. A 8% PAGE was run to assess end-filling.

The end-filled reaction mix was then heat inactivated at 65° C. for 15 minutes, cooled to room temperature and 1.5 µl Exonuclease I (20 U/µl) added. The reaction was incubated at 37° C. for 30 minutes and then heat inactivated at 80° C. for 15 minutes.

The mix was phenol:$CHCl_3$ extracted and the DNA ethanol precipitated. The amount of DNA was quantitated.

To generate an aptamer pool for screening, 25 ng of dsDNA was combined in a 100 µl reaction with 1-2 units Taq polymerase, 10 µl 10× Taq buffer, 2 µl 100 mM $MgSO_4$, 2 µl 10 mM dNTPs, 30 pmol of a biotinylated oligonucleotide as above and 30 pmol of a primer with the sequence as follows:

5'-GGGAGCTCAGAATAAACGCTCAA-3'    (SEQ ID NO. 5)

5 to 8 PCR cycles are required to amplify sufficient product for screening. The non-biotinylated strand is isolated by binding the DNA to streptavidin Sepharose followed, by NaOH treatment and HCl neutralisation.

Example 4

Generation of Individual Aptamers

A single colony was picked into 25 µl of lysis buffer (20 mM EDTA, 2 mM Tris-HCl pH 8.5, 1% Triton x-100). The colony was lysed by heating at 99° C. for 10 minutes, and then stored until ready at 4° C.

One microlitre of the cracked colony was mixed with 19 µl of PCR reaction mix (a master mix prepared by mixing 50 µl 10× Taq buffer, 10 µl 100 mM $MgSO_4$, 10 µl 10 mM dNTPs, 10 µl 10 µM M13 forward primer, 10 µl 10 [M M13 reverse primer, 2.5 µl Taq polymerase (2U/0) and 382.5 µl $H_2O$). Twenty five cycles of amplification were then performed.

One microlitre of this PCR was diluted 1/50 and used in a second PCR to prepare biotinylated aptamer (see example 3 for experimental details)

Example 5

Isolation of Aptamers that Bind to Targets in Fixed Tissue Sections-Production of an Aptamer (MTA R72) that Detects Malignant Mesothelioma Malignant mesothelioma of the pleura was used as a model system for the ability to isolate aptamers that detect malignant versus benign reactive mesotheliosis and/or fibrous pleuritis.

The differential diagnosis of malignant mesothelioma versus benign reactive mesotheliosis and/or fibrous pleuritis is difficult to make, both clinically and histologically. Whilst antibodies help to distinguish mesothelioma from adenocarcinoma, the diagnosis of benign mesotheliosis and malignant mesothelioma typically requires considerable expertise on the part of the pathologist who is reliant on a panel of antibodies and accurate clinical and radiological information. However, in some cases a definite conclusion still cannot be made and only clinical follow up will provide the final diagnosis.

(i) Mesothelioma Tissues

Cases of malignant mesothelioma were retrieved from the files of the Department of Anatomical Pathology, Flinders Medical Centre. All cases had been diagnosed by an expert in pleural pathology (Douglas W. Henderson, Flinders Medical Centre, Adelaide) by employing light microscopy, a panel of monoclonal antibodies routinely used in the laboratory for the differentiation between mesothelioma and adenocarcinoma (essentially as described in Moran, C. A., M. R. Wick, and S. Suster (2000) "The role of immunohistochemistry in the diagnosis of malignant mesothelioma" Semin Diagn Pathol. 17(3): p. 178-83, and in Ordonez, N. G. (2002) "Immunohistochemical diagnosis of epithelioid mesotheliomas: a critical review of old markers, new markers" Hum Pathol. 33(10): p. 953-67), and electron microscopy in selected cases. All cases were reviewed for adequacy of the tissue in the block. There were 18 cases of malignant mesothelioma, consisting of 11 epithelioid mesotheliomas, 4 sarcomatoid/desmoplastic mesotheliomas and 3 biphasic mesotheliomas. Also, 5 cases of benign mesotheliosis/fibrous pleuritis were included as negative controls.

(ii) Generating Aptamers as Histological Markers

An oligonucleotide library containing 45 random nucleotides was synthesised using standard procedures and purchased from a commercial supplier. A starting pool of $10^{14}$ oligonucleotides was screened in the first round of selection.

One to fifty micrograms of a chemically synthesised aptamer library of average size of 85 nucleotides containing a random sequence region of 45 bases in 0.2 ml binding buffer (0.15 M NaCl, 10 mM phosphate pH 7.4, 5 mM $MgCl_2$) was used.

Formalin fixed tissue sections (5 micron) were de-paraffinised in Histo-Clear II (National Diagnostics, USA) and washed through a series of graded alcohols before undergoing antigen retrieval at 121° C. in sodium citrate buffer pH 6.5 for 12 min, then left to cool for 2 hrs.

The aptamer library was heat denatured and allowed to slowly cool to room temperature over a period of thirty minutes. The library solution was then placed on the surface of the tissue section and allowed to incubate at room temperature for 4 hours to overnight in a humidified container.

The tissue section was then washed six times with five millilitres of binding buffer to remove unbound aptamers, the tissue section placed under a microscope and the tumourigenic target cell population recovered by scraping with a scalpel, fine needle or laser capture microscopy. Total nucleic acids were recovered from the excised tissue by proteinase K digestion and aptamers in the eluate were amplified by PCR using standard procedures.

The enriched aptamer pool was rebound to similar tissue sections and the process repeated. Typically 5 to 9 selection cycles were required. Individual aptamers were then isolated by standard cloning methods. Aptamers were screened against their target tissue as described below and selected based on their ability to bind only to the cells of interest.

(iii) Detecting Aptamer Bound to its Target

Tissue sections that had undergone antigen retrieval were equilibrated in binding buffer (1×PBS, 5 mM $MgCl_2$) and incubated overnight in a humidified chamber with 1-10 nM (final concentration) thermally equilibrated aptamer. The sections were thoroughly washed in binding buffer to remove unbound aptamer. Aptamer binding was detected using the Enzyme Labelled Fluorescence (ELF) kit (Molecular Probes, USA). Briefly, the biotinylated aptamer is bound by a streptavidin-alkaline phosphatase conjugate that in turn reacts with the ELF phosphatase substrate. This reaction produces an intensely fluorescent yellow green precipitate at the site of enzymatic activity. Sections were counterstained with Harris Haematoxylin for 30 seconds before mounting in aqueous medium and coverslipping.

(iv) A Target on all Invasive Malignant Mesothelioma Cells

Using the protocol described above, an aptamer (MTA R72) was isolated that appeared to bind only to malignant mesothelial cells but not to the surrounding stromal tissue.

The nucleotide sequence of MTA R72 was determined from the corresponding clone. The DNA sequence of the aptamer was as follows:

(SEQ ID NO. 6)
5'-GGGAGCTCAGAATAAACGCTCAAGGAACAGCAAGATACGGTCACCGA

ACATAGCGCACCACAGGCACATTCGACATGAGGCCCGGATC-3'

Figure 1B:
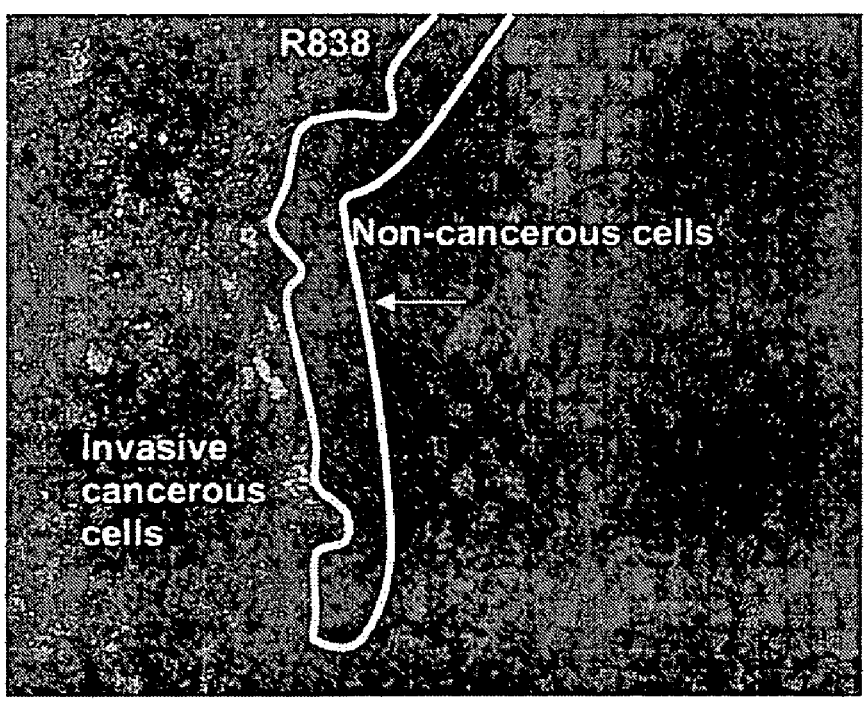
Figure 2A:
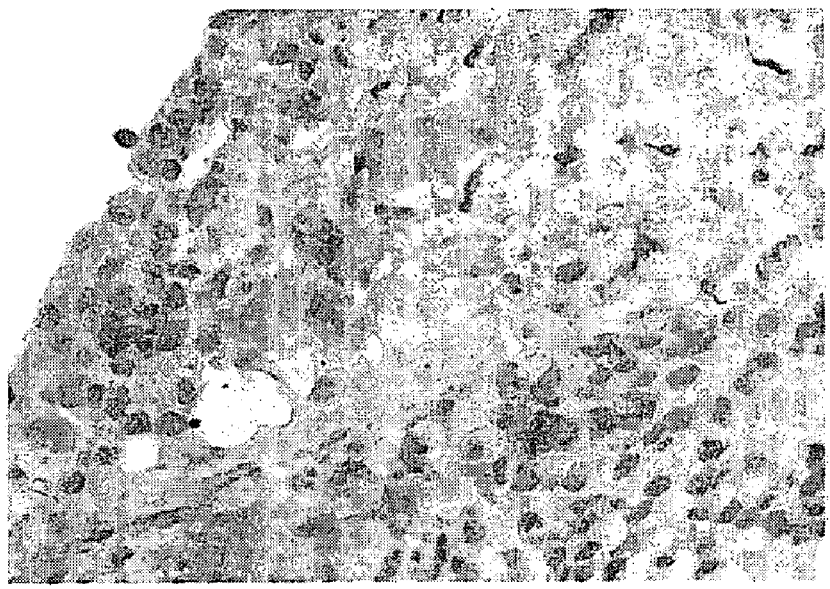
FIG. 2 shows staining of a biphasic mesothelioma tissue section in which the predominant epithelioid cells are positive as well as a few spindle shaped cells. The bright field image is shown in the top panel (FIG. 2A). The pattern of binding of aptamer MTA R72 is shown in the fluorescence image in the bottom panel (FIG. 2B). Both the spindle and the epithelioid malignant mesothelial cells show nuclear staining.
Figure 2B:
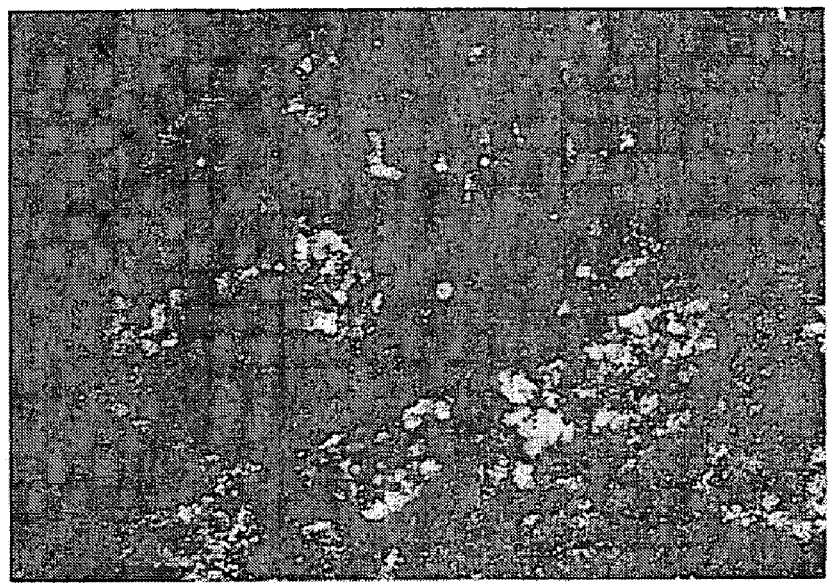
Figure 3:
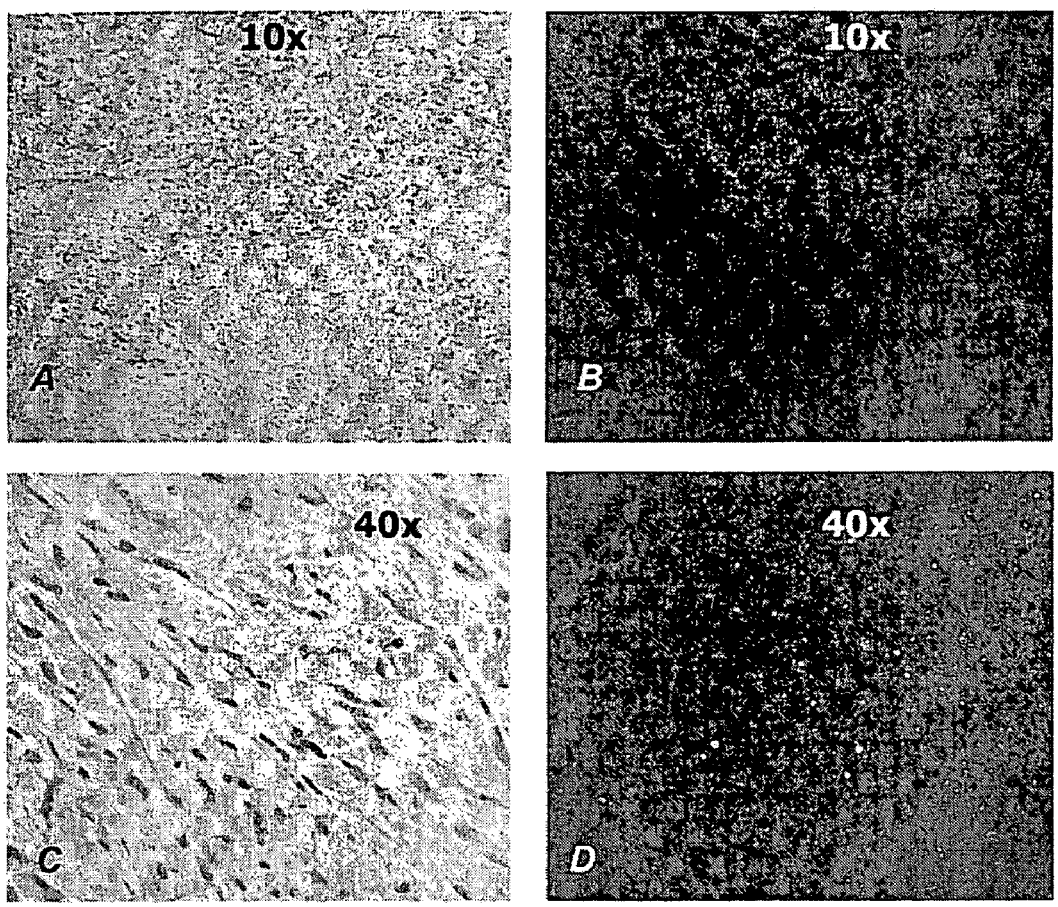
FIG. 3 shows staining of a desmoplastic mesothelioma tissue section with aptamer MTA R72. Panel A (bright field) and Panel B (fluorescence) are low magnification views. Panel C (bright field) and Panel D (fluorescence) are high power magnification views. The malignant spindle, cells bind MTA R72 whilst the surrounding stroma is negative. In this example, MTA R72 binding appears to be cytoplasmic rather than nuclear.

As shown in FIGS. 1 to 3 (both bright and fluorescent images shown), this aptamer positively identifies all cases of malignant mesothelioma examined thus far and binds to most of the malignant cells within the tumour. The staining pattern is predominantly nuclear in epithelioid and biphasic mesothelioma (in both epithelioid and sarcomatoid cells in the latter) as shown in FIGS. 1 and 2. The fluorescent staining is finely granular and clearly apparent at low power (i.e. using a 10× objective) examination. In desmoplastic mesotheliomas, the staining pattern appeared to be cytoplasmic rather than nuclear (FIG. 3), indicating a difference in target location between tumours.

Figure 4:
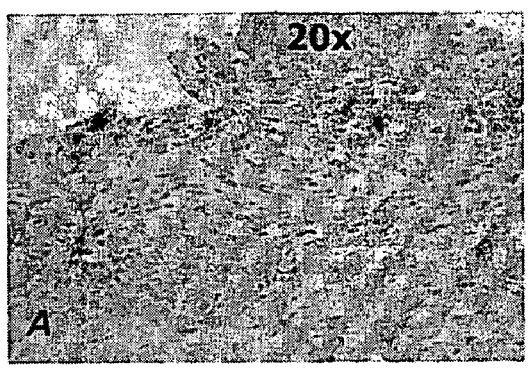
FIG. 4 shows an example of binding of aptamer MTA R72 to two cases (upper and lower panels respectively) of reactive mesotheliosis, in which only very focal and weak fluorescent staining is observed in reactive mesothelial cells (right panels).
Figure 4:
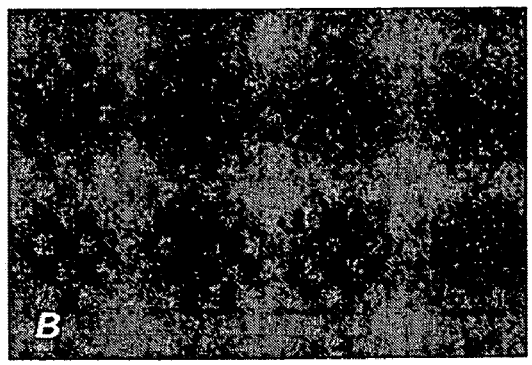
Figure 4:
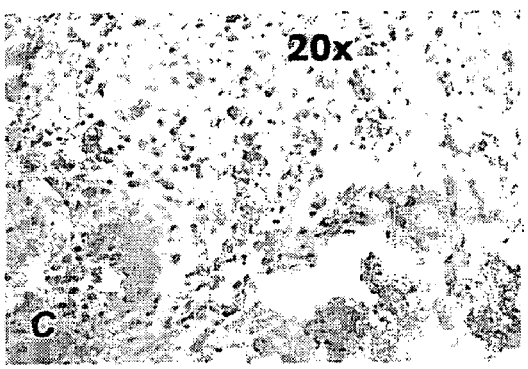
Figure 4:
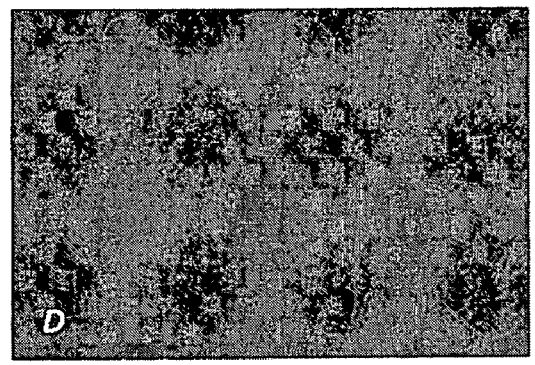

In contrast, no staining was detected in any of the reactive mesotheliosis/fibrous pleuritis cases as shown in FIG. 4.

All of the 18 cases of malignant mesothelioma showed positive labelling with this aptamer whilst none of the 5 reactive/inflammatory mesotheliosis cases exhibited labelling.

The data presented above show that it is possible to isolate aptamers on paraffin-embedded tissue sections that react exclusively with histologically and clinically confirmed malignant mesothelioma tissues, including the epithelioid, desmoplastic/sarcomatoid and biphasic subtypes. One aptamer (MTA R72) detects all cases of mesothelioma tested so far whilst all cases of reactive mesotheliosis/fibrous pleuritis have been negative. The differential diagnosis between mesothelioma and reactive mesothelial proliferations with cytological atypia is often difficult, but this aptamer detected differentially expressed targets on malignant cells.

Example 6

Further Studies on the Binding of Aptamer MTA R72 to Mesothelioma Tissue

The binding of aptamer MTA R72 to mesothelioma tissue was also tested for use in paraffin based Chromogenic Aptamer HistoChemistry. Tissue sections were prepared and stained with MTA-R72 as for example 5 except that a streptavidin horseradish peroxidase conjugate was used for visualising aptamer binding.

Figure 5:
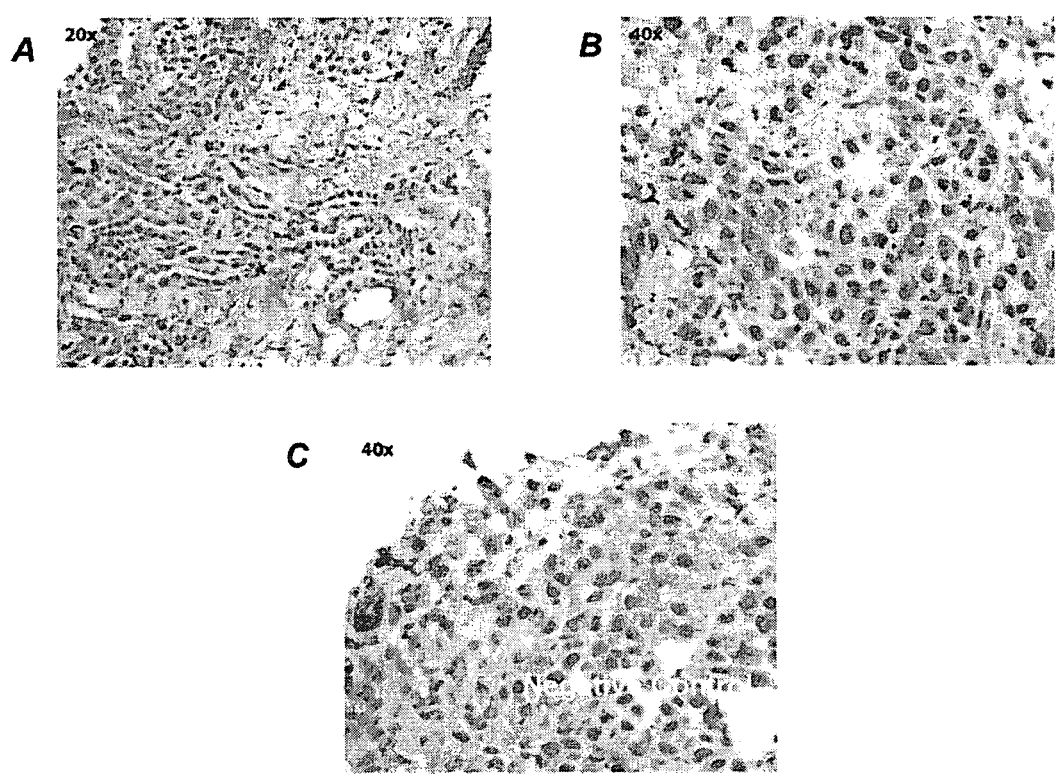
FIG. 5 shows aptamer MTA R72 staining of epithelioid mesothelioma cells using horseradish peroxidase and a chromogenic substrate to visualize bound aptamer. Panel A is a low power view (20×) of the tissue section showing areas of brown staining (aptamer binding) and regions (blue counterstain) where there is no aptamer binding. Panel B is high power view (40×). Panel C is a high power view of a negative control. High power views of the same section clearly show specific aptamer binding to malignant mesothelioma cells.

Aptamer MTA-R72 staining of mesothelioma shown in FIG. 5 shows brown enzyme product in nuclei of malignant cells in contrast to nonmalignant cells that have blue nuclei due to the counterstain.

These results show specific staining with MTA-R72 of mesothelioma cells was obtained, demonstrating that light microscopic Chromogenic Aptamer HistoChemistry may also be used for aptamer detection of mesothelioma cells.

Finally, it will be appreciated that various modifications and variations of the methods, polynucleotides and nucleic acid ligands of the invention described herein will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are apparent to those skilled in the art are intended to be within the scope of the present invention.

The invention claimed is:

1. An isolated polynucleotide comprising the nucleotide sequence according to SEQ ID NO:1.

2. An isolated polynucleotide variant of the nucleotide sequence according to SEQ ID NO.1, wherein the polynucleotide variant has at least 80% sequence identity over its full length to SEQ ID NO: 1.

3. An isolated polynucleotide that hybridises with the complement of the nucleotide sequence according to SEQ ID NO.1 under stringent hybridisation conditions, wherein the polynucleotide has at least 80% sequence identity over its full length to SEQ ID NO: 1.

4. An isolated polynucleotide according to claim 3, wherein the stringent hybridisation conditions include hybridisation in 4×SSC at 65° C. and washing in 0.1×SSC at 65° C.

5. An isolated polynucleotide according to claim 3, wherein the stringent hybridisation conditions include hybridisation in 50% formamide, 5×SSC and 1% SDS at 65° C. and washing in 0.2×SSC and 0.1% SDS at 65° C.

6. An isolated nucleic acid ligand that distinguishes a malignant mesothelial cell from a non-malignant mesothelial cell, wherein the nucleic acid ligand includes a nucleotide sequence according to SEQ ID NO:1 or a variant of the nucleotide sequence according to SEQ ID NO:1, wherein the variant has at least 80% sequence identity over its full length to SEQ ID NO: 1.

7. An isolated polynucleotide according to claim 1, wherein the polynucleotide forms a nucleic acid ligand that identifies at least one difference at the molecular level between two complex biological mixtures.

8. An isolated polynucleotide according to claim 7, wherein the polynucleotide forms a nucleic acid ligand that identifies at least one difference at the molecular level between a malignant mesothelial cell and a non-malignant mesothelial cell.

9. An isolated polynucleotide variant according to claim 2, wherein the polynucleotide variant has at least 90% sequence identity over its full length to SEQ ID NO: 1.

10. An isolated polynucleotide variant according to claim 2, wherein the polynucleotide variant has at least 95% sequence identity over its full length to SEQ ID NO: 1.

11. An isolated polynucleotide variant according to claim 2, wherein the polynucleotide variant has at least 98% sequence identity over its full length to SEQ ID NO: 1.

12. An isolated polynucleotide according to claim 3, wherein the polynucleotide has at least 90% sequence identity over its full length to SEQ ID NO: 1.

13. An isolated polynucleotide according to claim 3, wherein the polynucleotide has at least 95% sequence identity over its full length to SEQ ID NO: 1.

14. An isolated polynucleotide according to claim 3, wherein the polynucleotide has at least 98% sequence identity over its full length to SEQ ID NO: 1.

15. An isolated nucleic acid ligand according to claim 6, wherein the variant has at least 90% sequence identity over its full length to SEQ ID NO: 1.

16. An isolated nucleic acid ligand according to claim 6, wherein the variant has at least 95% sequence identity over its full length to SEQ ID NO: 1.

17. An isolated nucleic acid ligand according to claim 6, wherein the variant has at least 98% sequence identity over its full length to SEQ ID NO: 1.

* * * * *